United States Patent
Braff et al.

(10) Patent No.: US 6,692,952 B1
(45) Date of Patent: Feb. 17, 2004

(54) CELL ANALYSIS AND SORTING APPARATUS FOR MANIPULATION OF CELLS

(75) Inventors: Rebecca Braff, Boston, MA (US); Joel Voldman, Somerville, MA (US); Martha Gray, Arlington, MA (US); Martin Schmidt, Reading, MA (US); Mehmet Toner, Wellesley, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 324 days.

(21) Appl. No.: 09/710,032

(22) Filed: Nov. 10, 2000

Related U.S. Application Data

(60) Provisional application No. 60/164,643, filed on Nov. 10, 1999.

(51) Int. Cl.[7] .................................................. C12M 1/34
(52) U.S. Cl. ................................ 435/288.4; 435/288.5; 204/403.01; 204/403.13; 204/409; 204/450
(58) Field of Search .............................. 204/450, 400, 204/409, 403.01, 403.13, 412; 435/288.4, 288.5

(56) References Cited

U.S. PATENT DOCUMENTS

| | | | |
|---|---|---|---|
| 4,894,343 A | 1/1990 | Tanaka et al. | 435/301 |
| 5,506,141 A | 4/1996 | Weinreb et al. | 435/309.1 |
| 6,315,940 B1 * | 11/2001 | Nisch et al. | 435/287.1 |

FOREIGN PATENT DOCUMENTS

| | | |
|---|---|---|
| DE | 19712309 | 5/1998 |
| WO | 9931503 | 6/1999 |

OTHER PUBLICATIONS

Evans, J. et al., "Stable Mechanical Valve for In–Plane Fluid Control," *Transducers* (1999), Proceedings of the 10th International Conference on Solid–State Sensors and Actuators, Sendai, Japan.

Deshmukh, A. et al., "Continuous Micromixer with Pulsatile Micropumps," Solid–State Sensor and Actuator Workshop, Hilton Head Island, SC, Jun. 2000.

Farooqui M. et al., "Microfabrication of Submicron Nozzles in Silicon Nitride", *J. of Microelectromechanical Systems*, (1992) 1: 86–88.

Lin, L. et al., "Microbubble Powered Actuator", *Proceedings of Transducers* (1991): 1041–1044.

Papavasiliou, A. et al., "Electrolysis–Bubble Actuated Gate Valve," Solid–State Sensor and Actuator Workshop, Hilton Head Island, SC, Jun. 2000.

Sato, K. et al., "Individual and Mass Operation of Biological Cells using Micromechanical Silicon Deices," *J. of Sensors and Actuators*, (1990) A21–A23:948–953.

Tong, Q.Y., "Low Temperature Wafer Direct Bonding," *J. of Microelectromechanical Systems*, (1994) 3(1):29–35.

Yuan, H. et al., "The pumping effect of growing and collapsing bubbles in a tube," *J. of Micromechanics and Microengineering*, (1999) 9: 402–413.

* cited by examiner

*Primary Examiner*—David A. Redding
(74) *Attorney, Agent, or Firm*—Thomas J. Engellenner; Tram Anh T. Nguyen; Nutter McClennen & Fish LLP

(57) ABSTRACT

A cell analysis and sorting apparatus is capable of monitoring over time the behavior of each cell in a large population of cells. The cell analysis and sorting apparatus contains individually addressable cell locations. Each location is capable of capturing and holding a single cell, and selectively releasing that cell from that particular location. In one aspect of the invention, the cells are captured and held in wells, and released using vapor bubbles as a means of cell actuation. In another aspect of the invention, the cells are captured, held and released using electric field traps.

34 Claims, 27 Drawing Sheets

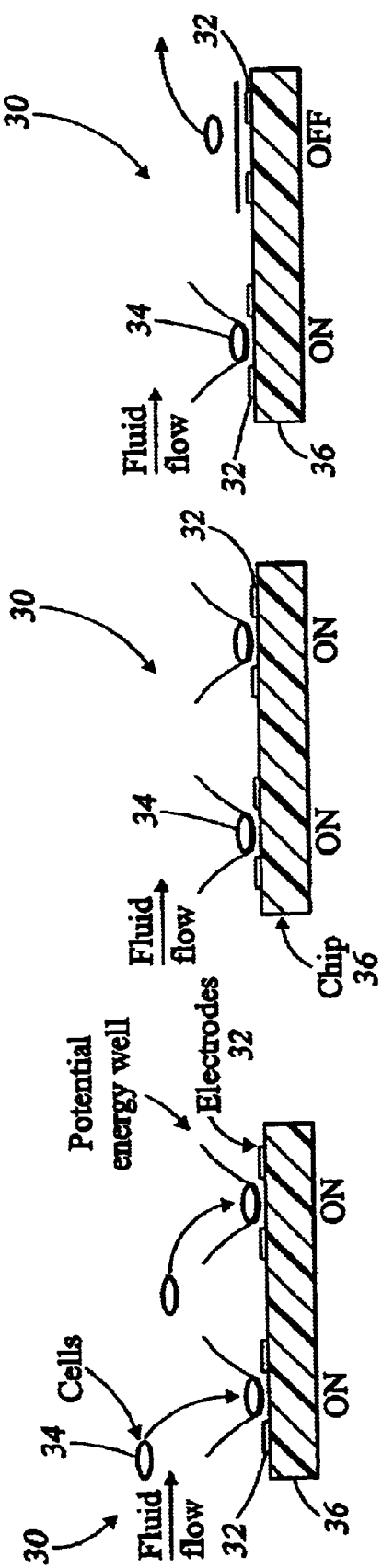

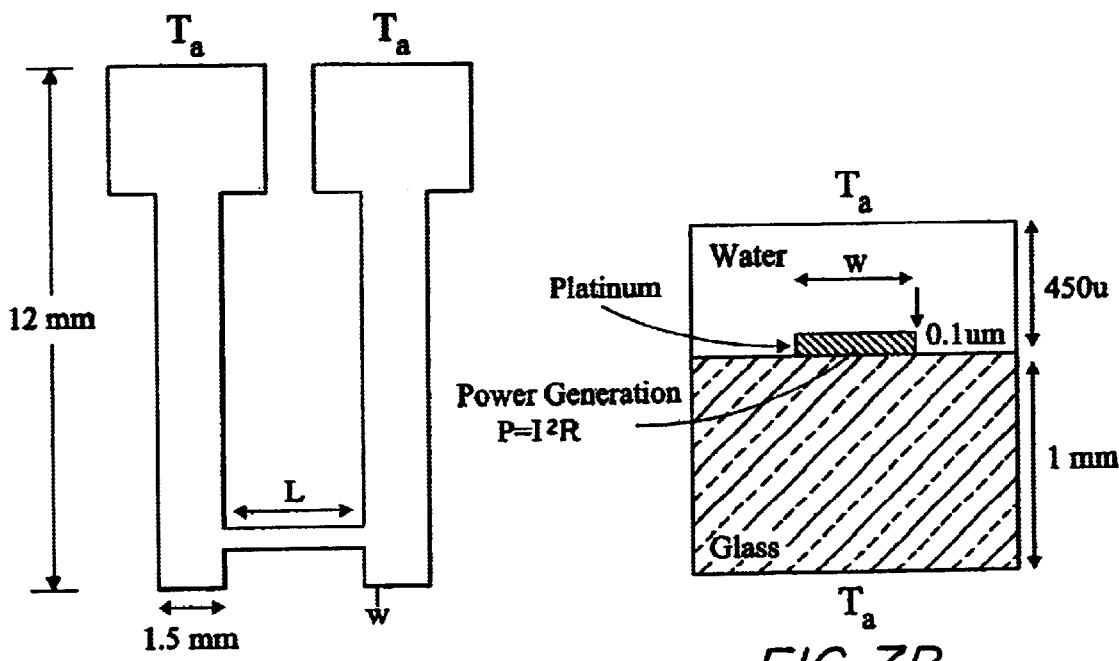
FIG. 7A
FIG. 7B
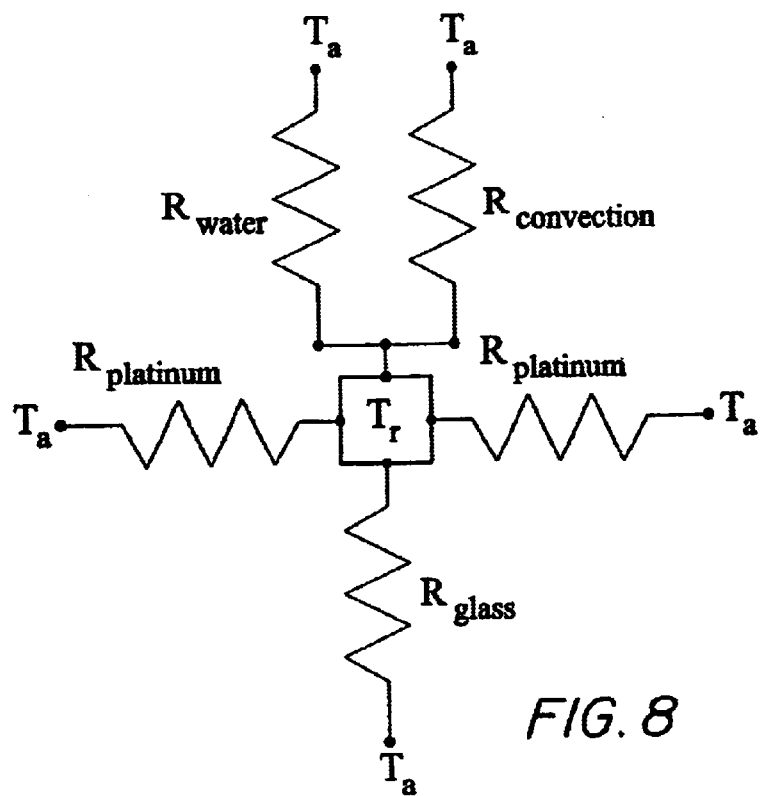
FIG. 8

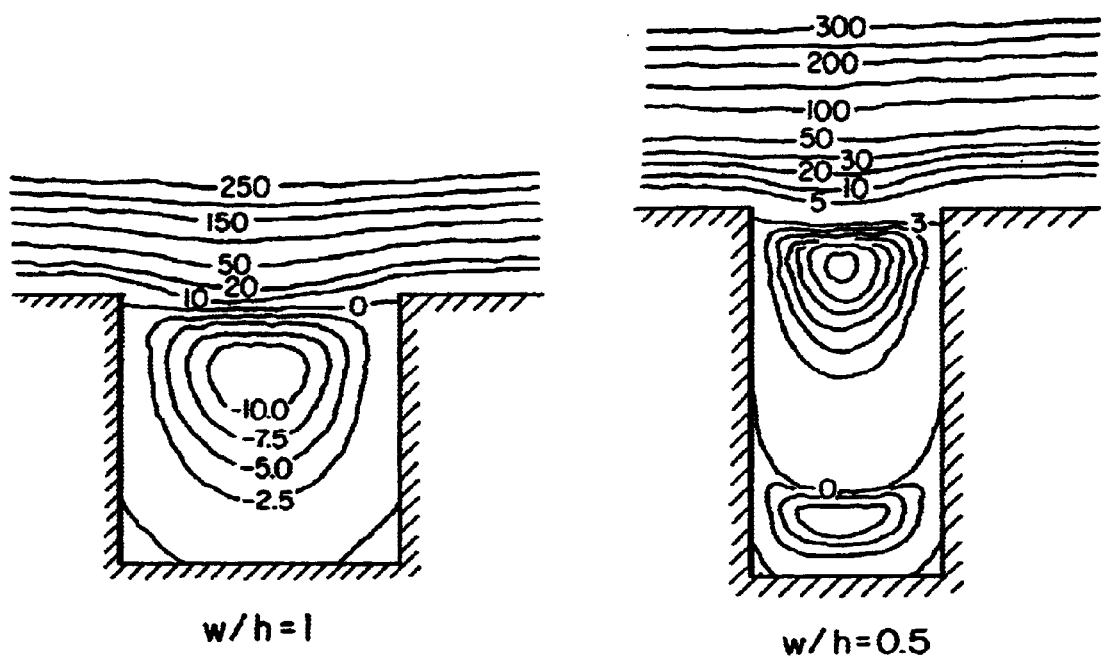
w/h=1  
FIG. 9A
w/h=0.5  
FIG. 9B
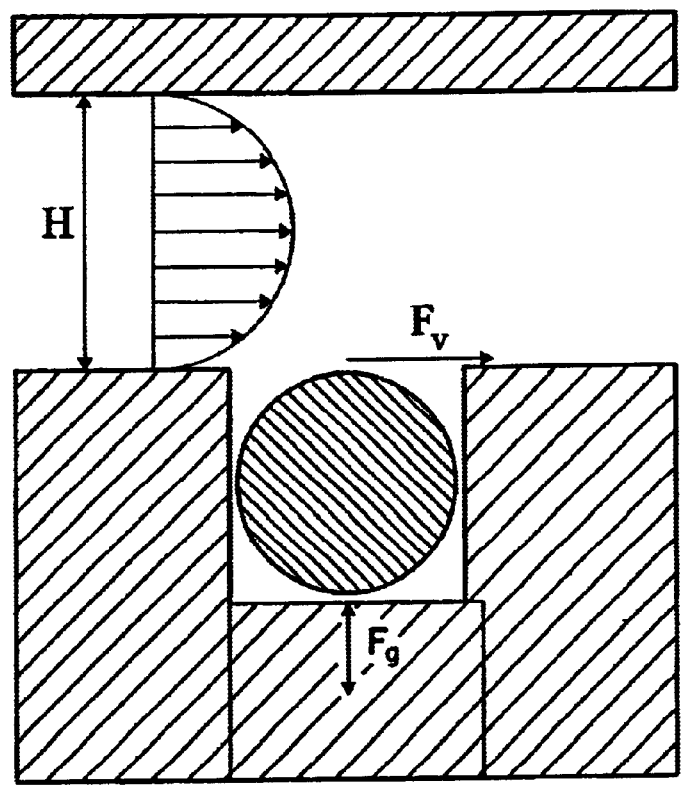
FIG. 10

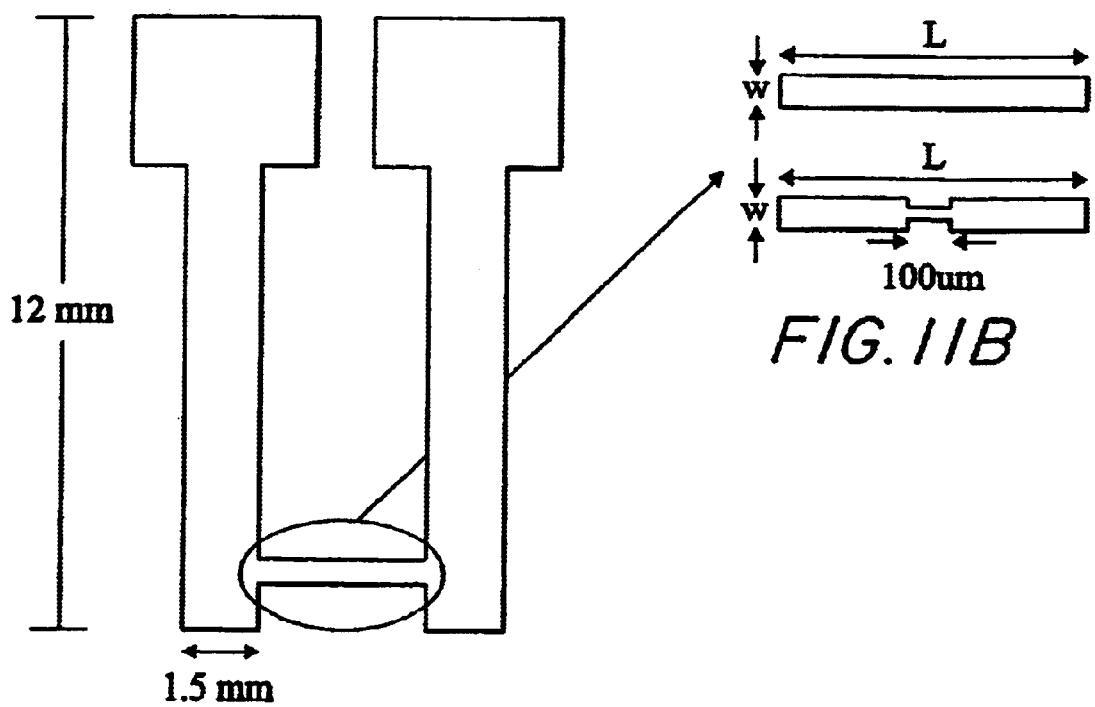
*FIG. 11A*
*FIG. 11B*
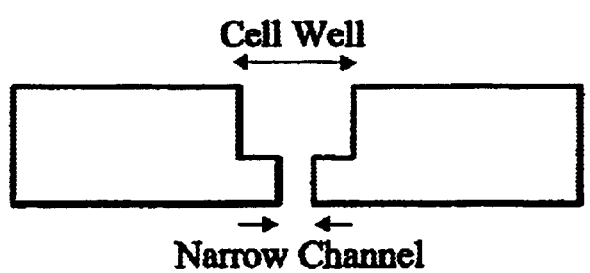
*FIG. 12A*
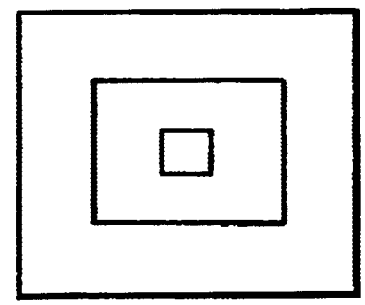
*FIG. 12B*

Mask 1

Mask 2

Mask 3

Mask 4

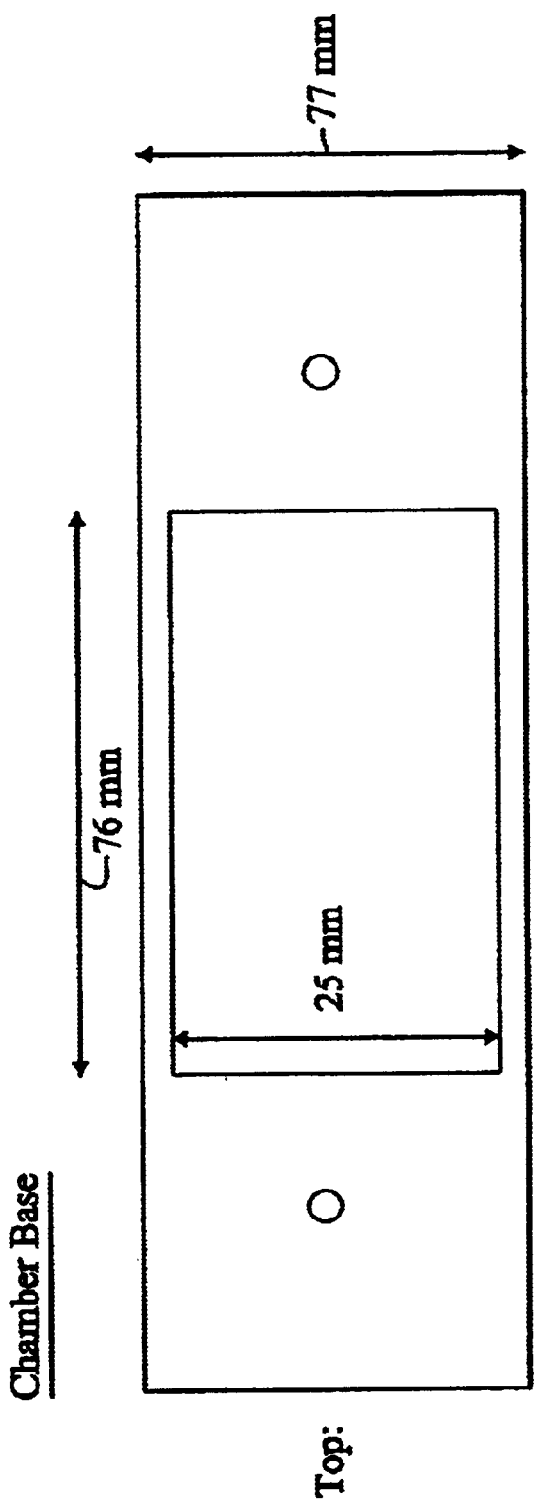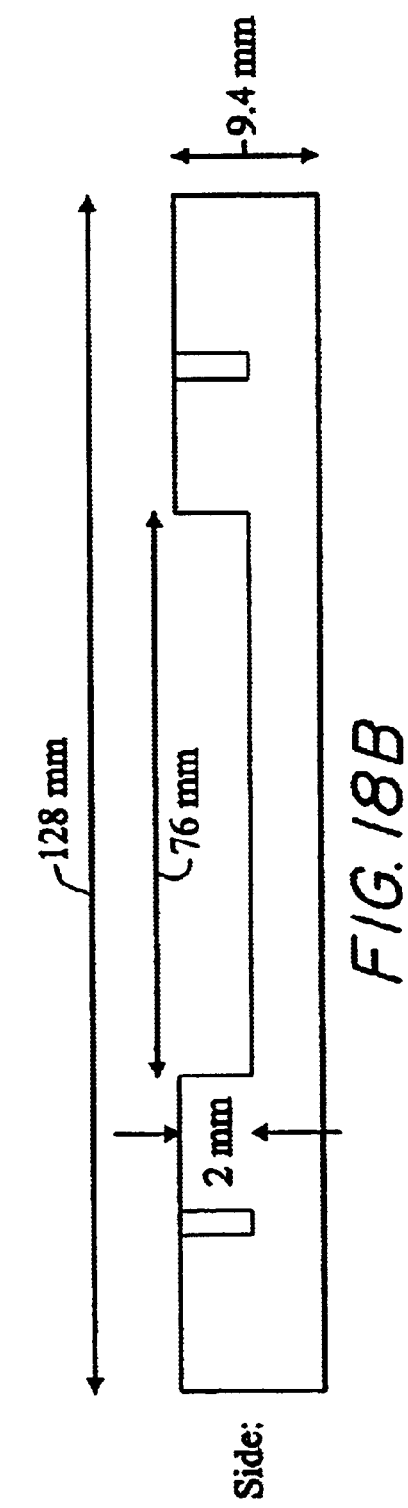

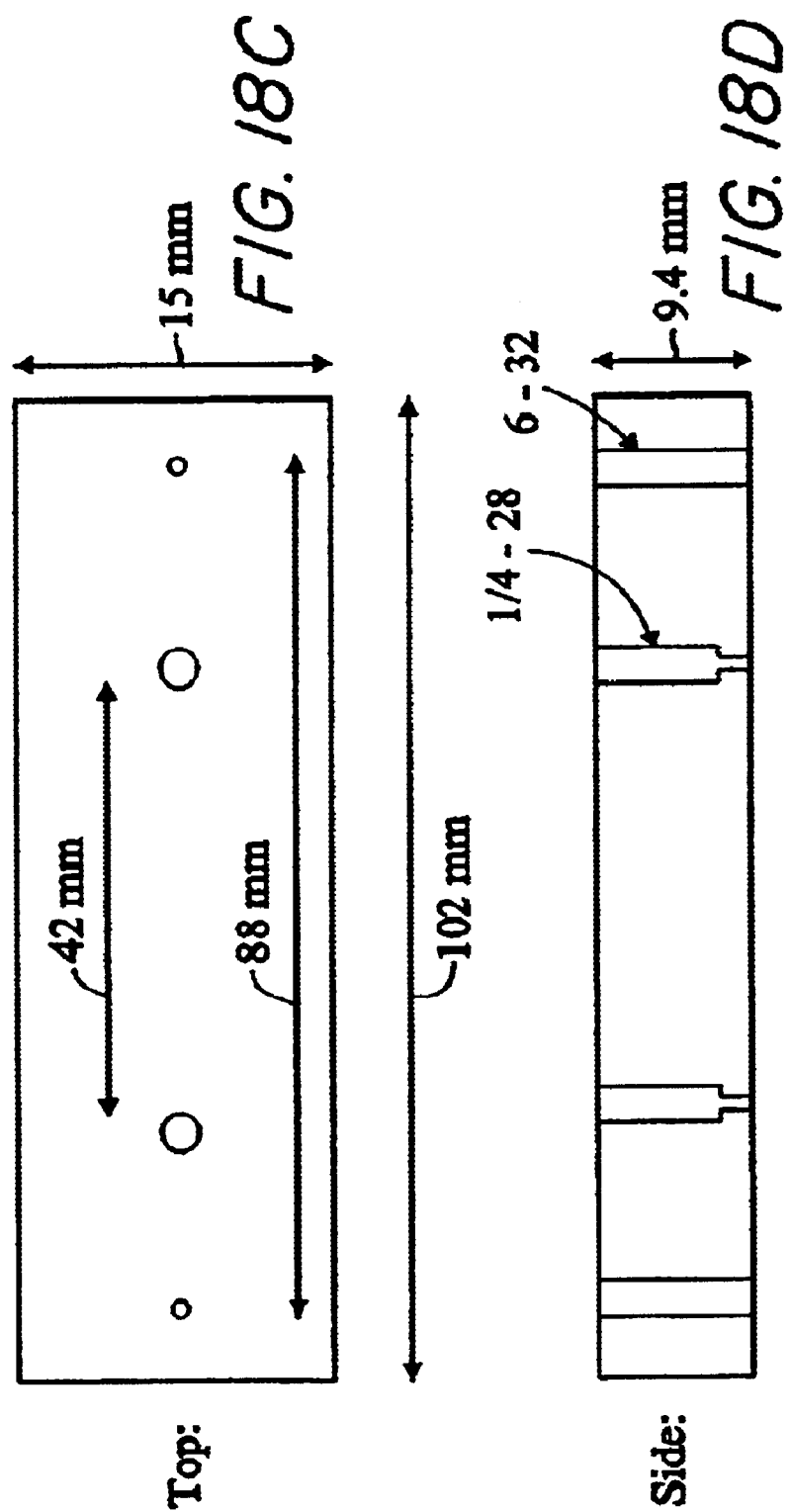

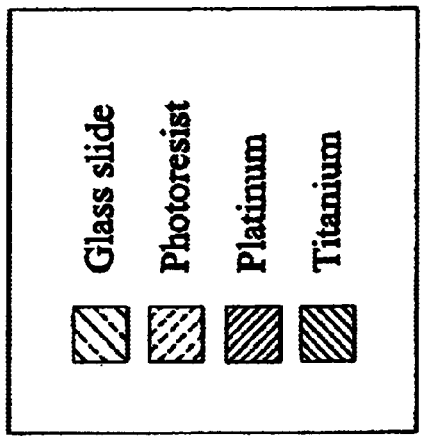
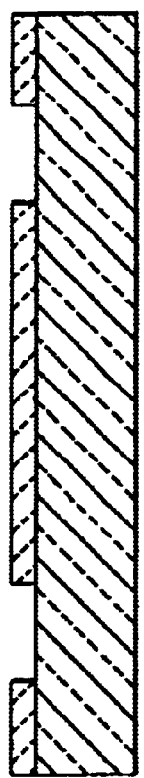
FIG. 19A Spin resist on glass slide and expose with mask 4
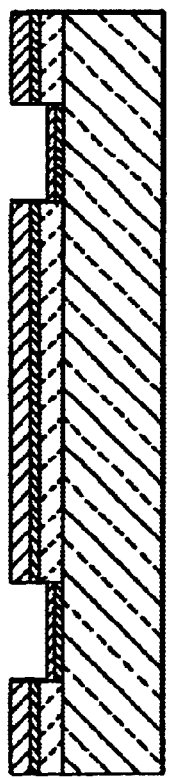
FIG. 19B Evaporate platinum and titanium
FIG. 19C Lift-off in acetone

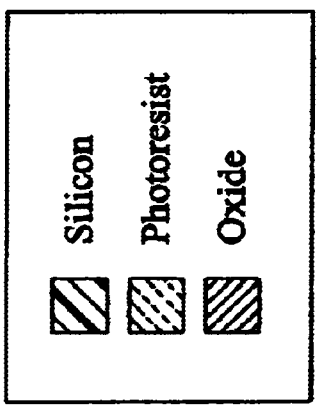
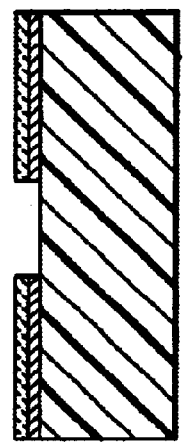
FIG. 20B
Expose with Mask 1, develop
FIG. 20D
Etch small trench using resist mask, strip resist
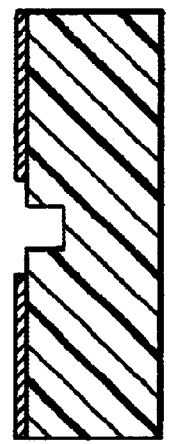
FIG. 20A
Grow thermal oxide, spin resist
FIG. 20C
Spin resist, Expose with Mask 2

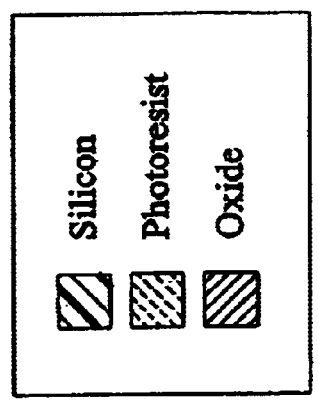
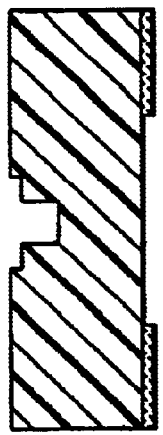
Etch wider trench using oxide mask
FIG. 20E
Spin resist on back of wafer, expose with Mask 3
FIG. 20F
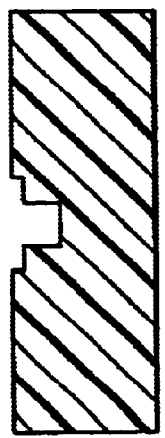
Timed etch through wafer to intersect
FIG. 20G
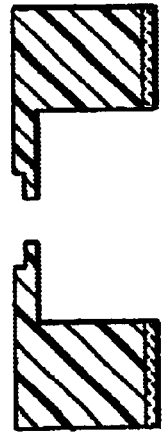
Finished wafer
FIG. 20H

Chip

Back

Slide

Front

CELL ANALYSIS AND SORTING APPARATUS FOR MANIPULATION OF CELLS

CROSS-REFERENCE TO RELATED APPLICATIONS

This application claims priority to U.S. provision application No. 60/164,643, which was filed on Nov. 10, 1999.

FIELD OF THE INVENTION

This invention relates to cell analysis and sorting devices and methods for manipulating cells using these devices. More particularly, the invention relates to a cell analysis and sorting apparatus that can capture and hold single cells at known locations and then selectively release certain of these cells. A method of manipulating the cells using the cell analysis and sorting apparatus is also provided.

BACKGROUND OF THE INVENTION

Many recent technological advances have enhanced the study of cellular biology and biomechanical engineering, most notably by improving methods and devices for carrying out cellular analysis. For example, in the past decade an explosion in the number of optical probes available for cell analysis has enabled an increase in the amount of information gleaned from microscopic and flow cytometric assays. Microscopic assays allow the researcher to monitor the time-response of a limited number of cells using optical probes. Flow cytometry, on the other hand, uses optical probes for assays on statistically significant quantities of cells for sorting into subpopulations.

However, these mechanisms alone are insufficient for time-dependent analysis. Microscopic assays can only track a few cells over time, and do not allow the user to track the location of individual cells. With flow cytometry, the user can only observe each cell once, and can only easily sort a cell population into three subpopulations. Flow cytometry techniques fail to provide for analysis of the same cell multiple times, or for arbitrary sorting of subpopulations. These kinds of bulk assay techniques produce mean statistics, but cannot provide the researcher with distribution statistics.

Advances in microsystems technology have also influenced many applications in the fields of cell biology and biomedical engineering. Scaling down to the micron level allows the use of smaller sample sizes than those used in conventional techniques. Additionally, the smaller size and ability to make large arrays of devices enables multiple processes to be run in parallel.

Integrated circuits have been fabricated on silicon chips since the 1950s, and as processing techniques improve, the size of transistors continues to shrink. The ability to produce large numbers of complex devices on a single chip sparked interest in fabricating mechanical structures on silicon as well. The range of applications for micro electromechanical systems (MEMS) is enormous. Accelerometers, pressure sensors, and actuators are just a few of the many MEMS devices currently produced. Another application of MEMS is in biology and medicine. Micromachined devices have been made for use in drug-delivery, DNA analysis, diagnostics, and detection of cell properties.

Manipulation of cells is another application of MEMS. For example, in the early 1990's, Sato et al. described in his paper, which is hereby incorporated by reference, *Individual and Mass Operation of Biological Cells using Microme-chanical Silicon Devices*, Sensors and Actuators, 1990, A21–A23:948–953, the use of pressure differentials to hold cells. Sato et al. microfabricated hydraulic capture chambers that were used to capture plant cells for use in cell fusion experiments. Pressure differentials were applied so that single cells were sucked down to plug an array of holes. Cells could not be individually released from the array, however, because the pressure differential was applied over the whole array, not to individual holes.

Bousse et al. in his paper, which is hereby incorporated by reference, *Micromachined Multichannel Systems for the Measurement of Cellular Metabolism*, Sensors and Actuators B, 1994, 20:145–150, described arrays of wells etched into silicon to passively capture cells by gravitational settling. Multiple cells were allowed to settle into each of an array of wells where they were held against flow due to the hydrodynamics resulting from the geometry of the wells. Changes in the pH of the medium surrounding the cells were monitored by sensors in the bottom of the wells, but the wells lacked a cell-release mechanism, and multiple cells were trapped in each well. Another known method of cell capture is dielectrophoresis (DEP). DEP refers to the action of neutral particles in non-uniform electric fields. Neutral polarizable particles experience a force in non-uniform electric fields which propels them toward the electric field maxima or minima, depending on whether the particle is more or less polarizable than the medium it is in. By arranging the electrodes properly, an electric field may be produced to stably trap dielectric particles.

Microfabrication has been utilized to make electrode arrays for cell manipulation since the late 1980s. Researchers have successfully trapped many different cell types, including mammalian cells, yeast cells, plant cells, and polymeric particles. Much work involves manipulating cells by exploiting differences in the dielectric properties of varying cell types to evoke separations, such as separation of viable from non-viable yeast, and enrichment of CD34+ stem cells from bone marrow and peripheral blood stem cells. More relevant work on trapping cells in various two- and three-dimensional microfabricated electrode geometries has been shown by several groups. However, trapping arrays of cells with the intention of releasing selected subpopulations of cells has not yet been widely explored. Additionally, DEP can potentially induce large temperature changes, causing not only convection effects but also profoundly affecting cell physiology.

These studies demonstrate that it is possible to trap individual and small numbers of cells in an array on a chip, but without the ability to subsequently manipulate and selectively release individual cells. This inability to select or sort based on a biochemical measurement poses a limitation to the kinds of scientific inquiring that may be of interest.

The currently available mechanisms for carrying out cell analysis and sorting are thus limited in their applications. There is thus a need for an improved method and apparatus for sorting and releasing large quantities of cells that can easily and efficiently be used. In addition, there is a need for an analysis and sorting device that allows the user to look at each cell multiple times, and to track many cells over time. Finally, there is a need for a cell sorter that lets the user know the cell locations, and to be able to hold and selectively release the cells so that the user can arbitrarily sort based on any aspect of the cells' characteristic during time-responsive assays.

SUMMARY OF THE INVENTION

The present invention provides a cell sorting apparatus that is capable of monitoring over time the behavior of each cell in a large population of cells. The cell analysis and sorting apparatus contains individually addressable cell locations. Each location is capable of capturing and holding a single cell, and selectively releasing that cell from that particular location. In one aspect of the invention, the cells are captured and held in wells, and released using vapor bubbles as a means of cell election. In another aspect of the invention, the cells are captured, held and released using electric field traps.

According to one aspect of the present invention, the cell analysis and sorting apparatus has an array of geometric sites for capturing cells traveling along a fluid flow. The geometric sites are arranged in a defined pattern across a substrate such that individual sites are known and identifiable. Each geometric site is configured and dimensioned to hold a single cell. Additionally, each site contains a release mechanism to selectively release the single cell from that site. Because each site is able to hold only one cell, and each site has a unique address, the apparatus allows the user to know the location of any particular cell that has been captured. Further, each site is independently controllable so that the user is able to arbitrarily capture cells at select locations, and to release cells at various locations across the array.

In one embodiment of the present invention, the geometric sites are configured as wells. As a fluid of cells is flown across the array of specifically sized wells, cells will fall into the wells and become trapped. Each well is sized and shaped to capture only a single cell, and is configured such that the cell will not escape into the laminar flow of the fluid above the well. The single cell can be held inside the well by gravitational forces. Each well can further be attached via a narrow channel to a chamber located below the well. Within the chamber is a heating element that is able to induce bubble nucleation, the mechanism for releasing the cell from the site. The bubble creates volume expansion inside the chamber which, when filled with fluid, will displace a jet of fluid out of the narrow channel and eject the cell out of the well. Fluid flow above the well will sweep the ejected cell away to be either collected or discarded.

In another embodiment of the present invention, the geometric sites are formed from a three-dimensional electric field trap. Each trap comprises four electrodes arranged in a trapezoidal configuration, where each electrode represents a corner of the trapezoid. The electric fields of the electrodes create a potential energy well for capturing a single cell within the center of the trap. By removing the potential energy well of the trap, the cell is ejected out of the site and into the fluid flow around the trap. Ejected cells can then be washed out and collected or discarded.

In yet another embodiment of the present invention, an integrated system is proposed. The system can be a microfabrication-based dynamic array cytometer ($\mu$DAC) having as one of its components the cell analysis and sorting apparatus previously described. To analyze a population of cells, the cells can be placed on a cell array chip containing a plurality of cell sites. The cells are held in place within the plurality of cell sites in a manner similar to that described above and analyzed, for example, by photometric assay. Using an optical system to detect fluorescence, the response of the cells can be measured, with the intensity of the fluorescence reflecting the intensity of the cellular response. Once the experiment is complete, the cells exhibiting the desired response, or intensity, may be selectively released into a cell sorter to be further studied or otherwise selectively processed. Such an integrated system would allow researchers to also look at the cell's time response.

Further features and advantages of the present invention as well as the structure and operation of various embodiments of the present invention are described in detail below with reference to the accompanying drawings.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

FIGS. 2A, 2B, and 2C show a process by which another embodiment of the present invention uses to capture, hold and release a single cell.

FIG. 7A shows a top view of a resistor of the present invention.

FIG. 7B shows a cross-section of the resistor of FIG. 7A.

FIG. 8 shows thermal resistances as seen by a heater of the present invention.

FIGS. 9A and 9B show flow lines for flow over rectangular cavities of different aspect ratios.

FIG. 10 shows a schematic of forces on a particle in a well.

FIG. 11A shows a top view of a heater of the present invention.

FIG. 11B shows a cross-section of the heater of FIG. 11A.

FIG. 12A shows a side view of a cell well of the present invention.

FIG. 12B shows a top-down view of the cell well of FIG. 12A.

FIG. 18A shows a top-down view of the chamber base of flow chamber of FIG. 16A and 16B.

FIG. 18B shows a side view of the chamber base of FIG. 18A.

FIG. 18C shows a top-down view of the chamber lid of flow chamber of FIG. 16A and 16B.

FIG. 18D shows a side view of the chamber lid of FIG. 18C.

FIGS. 19A–19C show a process of fabricating a glass slide of the present invention.

FIGS. 20A–20H show a process of fabricating a silicon wafer of the present invention.

DETAILED DESCRIPTION OF THE INVENTION

Figure 1A:
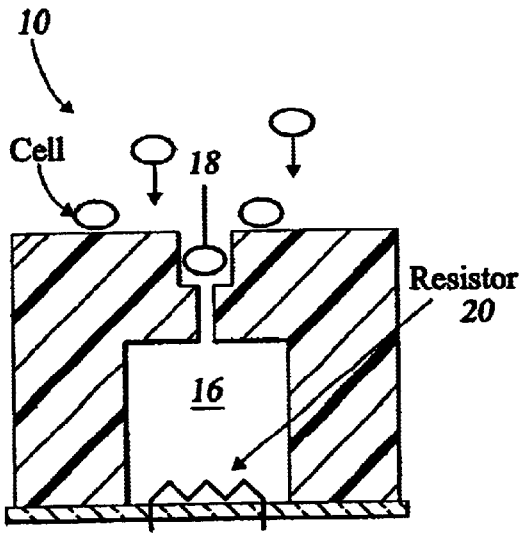
FIGS. 1A, 1B, 1C, and 1D show the mechanism by which one embodiment of the present invention uses to capture, hold and release a single cell.

FIGS. 1A–1D illustrate an exemplary system of the present invention. A cell site 10, shown in cross-section, contains a well 12 sized and shaped to hold a single cell 18. Connected to the bottom of the well 12 is a narrow channel 14 that opens into a chamber 16 situated below the well. In this particular example, the well 12 and narrow channel 14 are etched out of a silicon wafer. The silicon wafer is attached to a glass slide on which there is a platinum heater 20, and the alignment is such that the heater 20 is sealed inside the chamber 16, which is filled with a fluid such as water.

Figure 1B:
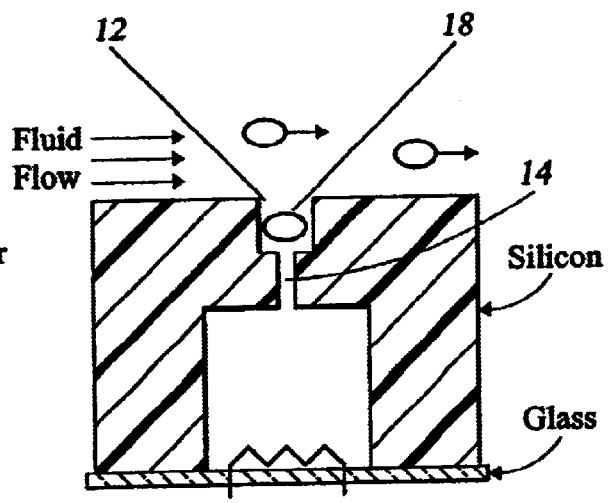

The well 12 functions as a capture and hold mechanism. In operation, fluid containing cells is flown over the top of the apparatus, and then the flow is stopped. As shown in FIG. 1A, the cells then settle and gravitational forces will allow one cell 18 to fall into and become trapped within the well 12. At this point the flow is started again, and the cell in the well is trapped while the cells not in wells are flushed away by convection. FIG. 1B shows how the well 12 is dimensioned and configured to hold only one cell 18 within the well 12 at a time. In addition, the well 12 is configured such that the cell 18 will not be swept out of the well due to laminar or fluid flow above.

Figure 1C:
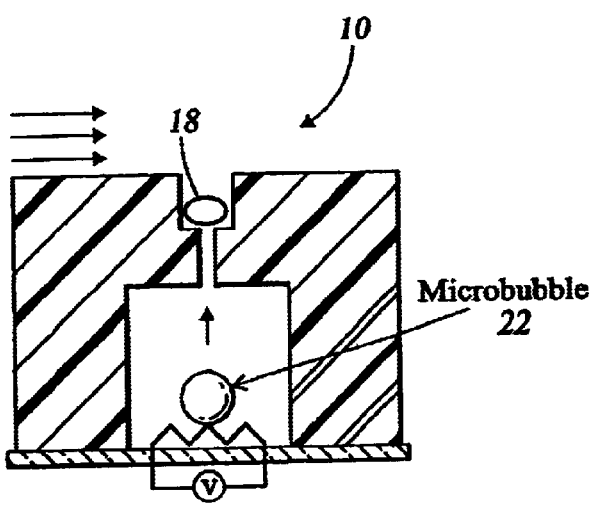
Figure 1D:
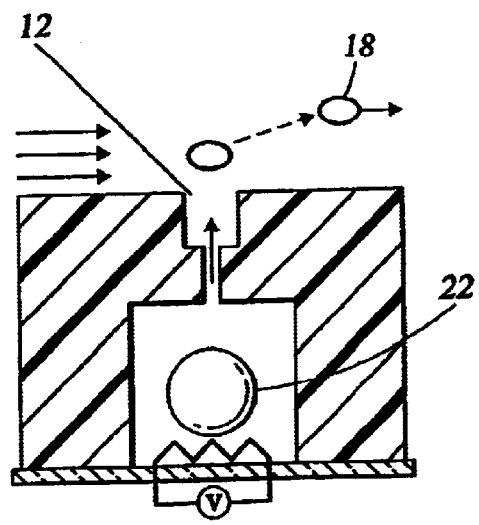

Experiments may be performed on the trapped cells, such as by adding a reagant. When the experiments are concluded, the cells exhibiting the desired characteristics may be selectively released from the wells. In this example, when it is desired to release cell 18 from the well 12, the operator can apply a voltage to the heating element 20 within the chamber 16. The heating element 20 is then heated to a temperature above the superlimit of the fluid contained within the chamber 16 to initiate vapor bubble nucleation at the surface of the heating element 20, as seen in FIG. 1C. In FIG. 1D, a microbubble 22 is formed inside the chamber, creating a volume displacement. By adjusting the voltage of the heating element 20, the operator can control the size of the microbubble 22. When the microbubble 22 is of sufficient size, the volume expansion in the chamber will displace a jet of fluid within the chamber 16 out of the narrow channel 14, ejecting the cell 18 out of the well 12. The released cell 18 can be swept into the fluid flow outside the well 12, to be later collected or discarded.

Figure 3A:
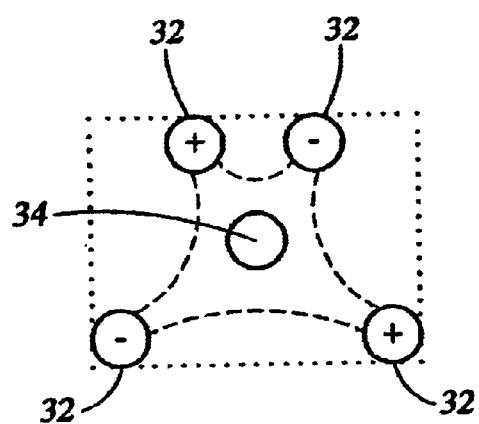
FIGS. 3A and 3B show a top-down view of the cell sorting apparatus of FIG. 2.
Figure 3B:
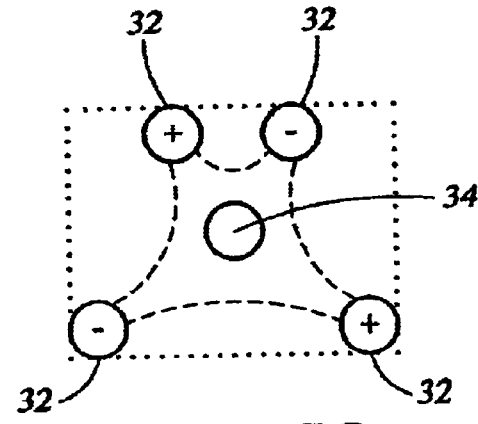
Figure 4:
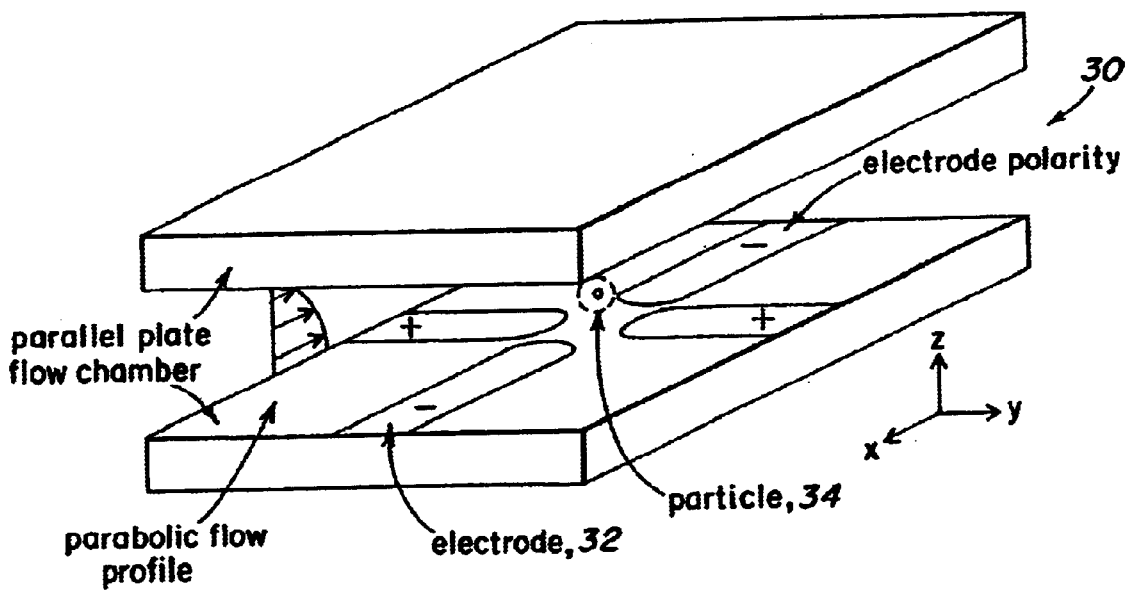
FIG. 4 shows an exploded view of the cell sorting apparatus of FIG. 2.

In another exemplary system of the present invention, the cell site 30 includes electric field traps. FIGS. 2A–2C show, in cross-section, two cell sites on a substrate such as a microfabricated chip 36. Each site includes a plurality of electrodes 32. Preferably, each cell site 30 contains four electrodes, positioned in a trapezoidal configuration, as seen in FIGS. 3A and 3B. The cell site 30 is configured and positioned such that only one cell can be held within the site. The electrodes 32 create a non-uniform electric field trap within which a single cell 34 can be held and subsequently released. FIG. 4 illustrates how the location and polarity of the electrodes 32 can create an electric field trap for capturing the cell 34.

In use, cells in fluid medium flow over the cell sites 30, as shown in FIG. 2A. By adjusting the electric field of each electrode 32, a potential energy well can be created within each cell site 30. The potential energy well is of sufficient strength to capture a single cell 34 traveling along the fluid flow and to hold the cell 34 within the center of the trap, as seen in FIG. 2B. When the operator selects to release a cell 34, he can adjust the electric fields of the electrodes 32 forming the trap. FIG. 2C shows how this in turn removes the potential energy well, releasing the cell 34 back into the fluid flow. The cell 34 can then be collected or discarded.

The electrodes forming the electric field trap are preferably thin-film poles formed of gold. This creates a three-dimensional electric field trap that is effective in holding a cell against the laminar flow of the fluid surrounding the electrodes. Further, while only one or two cell sites are illustrated, it is understood that the drawings are merely exemplary of the kind of site that can be included in the cell sorting apparatus of the present invention. The cell sorting apparatus can contain anywhere from a single cell site to an infinite number of cell sites, for sorting mass quantities of cells. Moreover, while the embodiments herein are described as holding cells, it is understood that what is meant by cells includes biological cells, cellular fragments, particles, biological molecules, ions, and other biological entities.

Figure 5:
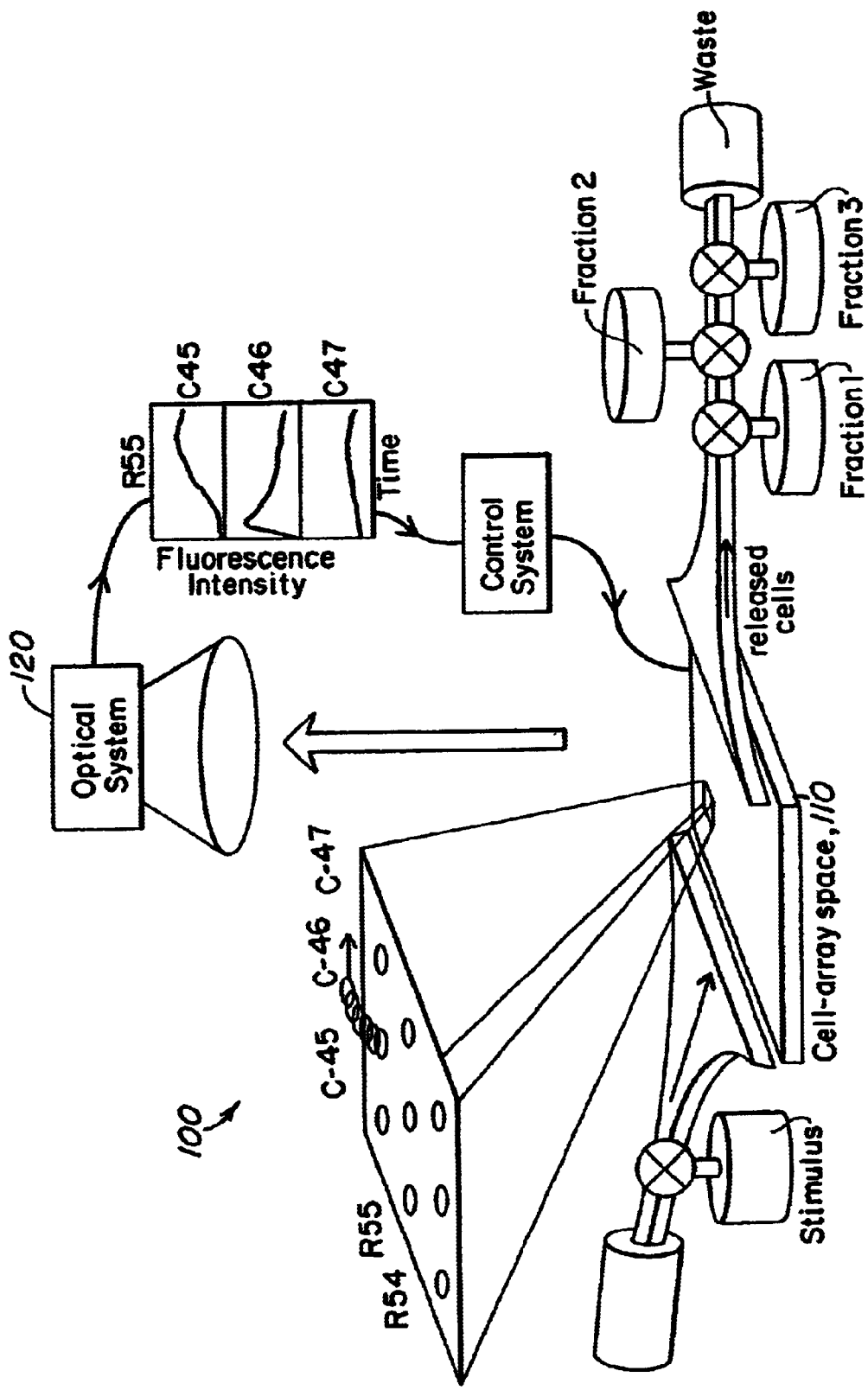
FIG. 5 shows an exploded view of yet another embodiment of the present invention in which a cell sorting apparatus is integrated into a fluorescence-detecting system.

Because the cell sorting apparatus of the present invention allows the operator to know the location of each cell in the array of cell sites, the operator is able to manipulate the cells and arbitrarily sort the cells based on their characteristic under time-responsive assays. One such method contemplates using scanning techniques to observe dynamic responses from cells. As shown in FIG. 5, an integrated cellular analysis system 100 is proposed in which cells are tested using light-emitting assays to determine the cell's response to stimuli over time. The integrated system can be a microfabrication-based dynamic array cytometer ($\mu$DAC). The tested cells are placed on a cell array chip 110 similar to the cell sorting apparatus above, to be held in place within the plurality of cell sites, such as those described above. Using an optical system 120 to detect fluorescence, the response of the cells can be measured, with the intensity of the fluorescence reflecting the intensity of the cellular response. Once the experiment is complete, the cells exhibiting the desired response, or intensity, may be selectively released, to be collected or later discarded. Such an integrated system would allow researchers to look at the cell's time response.

Any light-emitting assay in which the cell's response may vary in time is suited for study using this proposed system. It is ideally suited for finding phenotype inhomogeneities in a nominally homogeneous cell population. Such a system could be used to investigate time-based cellular responses for which practical assays do not currently exist. Instead of looking at the presence/absence or intensity of a cell's response to stimulus, the researcher can look at its time response. Furthermore, the researcher can gain information about a statistically significant number of cells without the potential of masking important differences as might occur in a bulk experiment. Specific applications may include the study of molecular interactions such as receptor-ligand binding or protein-protein interactions. Signal transduction pathways, such as those involving intracellular calcium, can also be investigated.

An advantage of the proposed integrated system is that the full time-response of all the cells can be accumulated and then sorting can be performed. This is contrasted with flow cytometry, where each cell is only analyzed at one time-point and sorting must happen concurrently with acquisition. Geneticists can look at gene expression, such as with immediate-early genes, either in response to environmental stimuli or for cell-cycle analysis. Another large application area is drug discovery using reporter-gene based assays. The integrated system can also be used to investigate fundamental biological issues dealing with the kinetics of drug interactions with cells, sorting and analyzing cells that display interesting pharmacodynamic responses. Another application is looking at heterogeneity in gene expression to investigate stochastic processes in cell regulation. Finally, once temporal responses to certain stimuli are determined, the integrated system can be used in a clinical setting to diagnose disease and monitor treatment by looking for abnormal time responses in patients' cells.

One objective of the present invention is to provide a cell analysis and sorting apparatus which uses hydraulic forces to capture individual cells into addressable locations, and can utilize microbubble actuation to release these individual cells from their locations. In developing this apparatus, it was necessary to model and understand many physical phenomena, not the least important of which includes the theory behind bubble nucleation on micro-heaters. Further, it was necessary to design a device with the proper dimensions so that single particles, or cells, could be held in wells against a flow. Biological cells were not used in these experiments, as polystyrene microspheres of the same dimensions were thought to be more robust for testing purposes. The fabrication process had to be designed in order to build chips with the desired attributes, and various problems which arose needed to be resolved. Finally, it was necessary to understand the heating of the resistors so that sufficiently high temperatures could be reached.

Under the theory of bubble nucleation, pool boiling takes place when a heater surface is submerged in a pool of liquid. As the heater surface temperature increases and exceeds the saturation temperature of the liquid by an adequate amount, vapor bubbles nucleate on the heater. The layer of fluid directly next to the heater is superheated, and bubbles grow rapidly in this region until they become sufficiently large and depart upwards by a buoyancy force. While rising the bubbles either collapse or continue growing depending on the temperature of the bulk fluid.

There are two modes of bubble nucleation: homogeneous and heterogeneous. Homogeneous nucleation occurs in a pure liquid, whereas heterogeneous nucleation occurs on a heated surface.

In a pure liquid containing no foreign objects, bubbles are nucleated by high-energy molecular groups. According to kinetic theory, pure liquids have local fluctuations in density, or vapor clusters. These are groups of highly energized molecules which have energies significantly higher than the average energy of molecules in the liquid. These molecules are called activated molecules and their excess energy is called the energy of activation. The nucleation process occurs by a stepwise collision process that is reversible, whereby molecules may increase or decrease their energy. When a cluster of activated molecules reaches a critical size, then bubble nucleation can occur.

Figure 6:
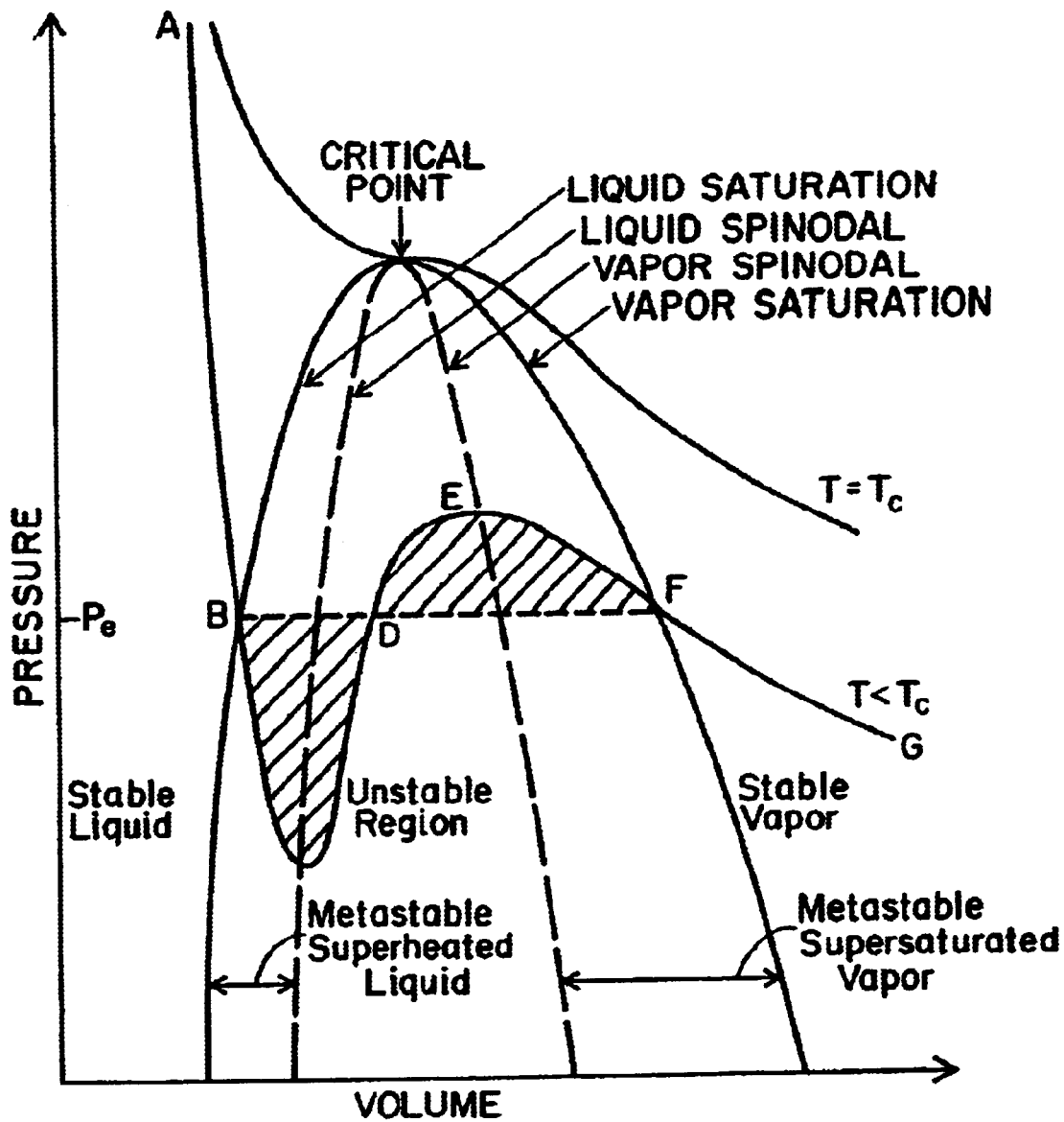
FIG. 6 is the thermodynamic pressure-volume diagram for water.

In order to determine at what temperature water will begin to boil in the homogeneous nucleation regime, it was useful to know the thermodynamic superheat limit of water. FIG. 6 is the thermodynamic pressure-volume diagram for water, which shows a region of stable liquid to the far left, stable vapor to the far right, metastable regions, and an unstable region in the center of the dashed curve. The dashed line is called the spinodal, and to the left of the critical point represents the upper limit to the existence of a superheated liquid. Along this line, Equation (1-1) holds true, and within the spinodal, Equation (1-2) applies.

$$\left(\frac{\partial P}{\partial v}\right)_T = 0 \tag{1-1}$$

$$\left(\frac{\partial P}{\partial v}\right)_T > 0 \tag{1-2}$$

The van der Waals and Berthelot equations of state were used to calculate the superheat limit of water.

$$\left(P + \frac{a}{T^n v^2}\right)(v - b) = RT \tag{1-3}$$

Where v is the specific volume, R is the gas constant, and a and b are constants. n=0 for the van der Waals equation, n=1 for the Berthelot equation, and n=0.5 for the modified Berthelot equation. a and b were computed using Equation (1-3), given the fact that at the critical point, Equations (1-4) and (1-5) are true.

$$\left(\frac{\partial P}{\partial v}\right)_{T_{cr}} = 0 \tag{1-4}$$

$$\left(\frac{\partial^2 P}{\partial v^2}\right)_{T_{cr}} = 0 \tag{1-5}$$

Using the above equations, the thermodynamic superheat limit of water was computed. The results are shown below in Table 1.

TABLE 1

Thermodynamic superheat limit of water calculated with 3 equations of state.

| Equation of State | $T/T_{cr}$ ($T_{cr}$ = 647° K.) | Superheat Limit (° C.) |
|---|---|---|
| Van der Waals | 0.844 | 273 |
| Modified Berthelot | 0.893 | 305 |
| Berthelot | 0.919 | 322 |

These values represent the temperature above which homogeneous nucleation must begin.

A kinetic limit of superheat may also be computed using the kinetic theory of the activated molecular clusters. The kinetic limit of superheat for water is about 300° C.

When liquid is heated in the presence of a solid surface, heterogeneous nucleation usually occurs. In this regime, bubbles typically nucleate in cavities (surface defects) on the heated surface. The degree of superheat necessary to nucleate a bubble in a cavity is inversely dependent on the cavity radius, as shown in Equation (1-6).

$$T_w - T_{sat} = \frac{2\sigma T_{sat}}{h_{lv}\rho_v r_c} \quad (1\text{-}6)$$

Where $T_w$ is the surface temperature, $T_{sat}$ is the saturation temperature (100° C. for water), $\sigma$ is the surface tension, $h_{fg}$ is the latent heat of vaporization, $\rho_v$ is the vapor density, and $r_c$ is the cavity radius. For example, the surface temperature necessary to nucleate bubbles in water with a surface that has a 1 $\mu$m cavity radius is about 133° C. For a 0.1 $\mu$m cavity radius the temperature to nucleate a bubble is about 432° C., well above the highest thermodynamic water superheat limit of 322° C.

Accordingly, for surfaces with cavity sizes well below 1 $\mu$m, it is likely that homogeneous nucleation will occur since the liquid will reach the superheat limit before a bubble nucleates in a cavity. Micromachined surfaces tend to have very smooth surfaces. For instance, the platinum resistors are only 3–6 $\mu$m wide, and 0.1 $\mu$m thick, so it is unlikely that cavities will exist on the surface which are large enough for heterogeneous nucleation to occur. The largest likely nucleation cavity would be the thickness of the resistor, which is 0.1 $\mu$m, and results in a boiling temperature for heterogeneous nucleation above the thermodynamic superheat limit as shown above. Thus, it was assumed that homogeneous nucleation was the most likely method of bubble nucleation to occur for the resistors of this invention.

However, when platinum films are annealed, thermal grooving and agglomeration can take place at the grain boundaries. A groove will develop on the surface of a hot polycrystalline material where a grain boundary meets the surface. As the surface gets hotter, the grooves deepen, initiating holes, and the platinum begins the process of balling up in order to reduce surface area. This process is called agglomeration. The agglomeration rate is insignificant at anneal temperatures below 700° C. However, for a 600° C. anneal of platinum for 1 hour, the onset of agglomeration can cause small voids in the platinum with radii of up to about 0.5 $\mu$m. In this case, heterogeneous nucleation would be possible at a temperature of about 166° C.

Next, it was desirable to predict the electrical current necessary to achieve a certain temperature of the resistor. The schematic and boundary conditions for this resistor model are shown in FIGS. 7A and 7B. For the cross-sectional slice through the resistor (7B), the water above the heater was 450 $\mu$m thick, corresponding to the height of the silicon chamber containing the water. It was assumed that the ambient temperature was maintained at the top of the water in the well since above this there was silicon with water at the ambient temperature flowing over the top of it. The bottom of the glass slide was also assumed to be at the ambient temperature since it was contacting a surface at the ambient temperature. The resistor was about 10,000 times thinner than the glass slide and had ohmic heating, or power generation equal to $I^2R$ for the entire volume of the resistor.

First, the characteristic time for the heat to conduct through the two bounding surfaces was calculated using Equation (1-7).

$$\tau \approx \frac{L^2}{\alpha} \quad (1\text{-}7)$$

Where L is the characteristic length for conduction and $\alpha$ is the thermal diffusivity of the material.

Using this relation, it was found that the characteristic time for conduction through 1 mm of glass was about 2.3 seconds. Similarly, the characteristic time for conduction through 450 $\mu$m of water was 1.38 seconds. Accordingly, for this system the time to reach steady state would be about four times greater than the highest characteristic time, about 9 seconds. As established above, homogeneous bubble nucleation was likely to occur, which is a molecular process and thus may be assumed to be approximately instantaneous. The time for a bubble to nucleate was therefore far shorter than the 9 seconds necessary for the system to reach steady state, so steady state conditions are unlikely to be achieved before the bubble nucleates.

It was then necessary to determine the dominant modes of heat transfer from the resistor to its surroundings. The purpose of this model was to predict the temperature of the heater for a given current, before the onset of boiling. For this model, heat transfer due to radiation was neglected.

A lumped model approach was taken for this analysis. This approximation was checked by computing the Biot number for the resistor.

$$Bi = \frac{ht}{k_{Pt}} = 7 \times 10^{-9} \ll 1 \quad (1\text{-}8)$$

Where t is the platinum resistor thickness (0.1 $\mu$m) and $k_{pt}$ is the thermal conductivity of platinum (71.5 W/mK). It was assumed in this model a heat transfer coefficient of h=5W/m²K as a high bound for natural convection. The Biot number measures the ratio of internal conduction resistance to external convection resistance. Since the Biot number was much less than unity, the lumped body approximation was used and an assumption was made that the entire resistor was at a uniform temperature.

FIG. 8 shows the thermal resistances between the resistor and the ambient temperature. For the purpose of this order of magnitude estimate of the heat transfer mechanisms, steady state conditions were used in determining thermal resistances. First, the thermal resistance due to convection through the water was computed. For this case it was assumed there was natural convection since the water above the heater was stagnant, and boiling was not occurring. The thermal resistance due to convection was calculated below.

$$R_{convection} = \frac{1}{hA} = \frac{1}{hwL} = 6.67 \times 10^7 \frac{K}{W} \quad (1\text{-}9)$$

Where w is the resistor width (3 $\mu$m) and L is the resistor length (1000 $\mu$m).

Next the thermal resistance due to conduction through the platinum resistor, glass slide, and water were computed. The resistance due to conduction was given by:

$$R_{conduction} = \frac{L}{kA} \quad (1\text{-}10)$$

Where L is the length through which heat conducts, and A is the cross-sectional area. For the platinum, the length through which heat conducts was very long (12 mm) and the cross-sectional area was very small, resulting in a high thermal resistance:

$$R_{platinum} = \frac{L_{Pt}}{k_{Pt}tw} = 5.4 \times 10^8 \frac{K}{W} \quad (1\text{-}11)$$

Where t is the platinum film thickness (0.1 $\mu$m), $L_{pt}$ is the length through which heat conducts (12 mm), w is the width of the resistor (3 $\mu$m), and $k_{pt}$ is the conductivity of platinum (71.5 W/mK). Similarly, the thermal resistances of the glass and water were computed.

$$R_{glass} = \frac{L_g}{k_g Lw} = 4.1 \times 10^5 \frac{K}{W} \quad (1\text{-}12)$$

$$R_{water} = \frac{L_w}{k_g Lw} = 2.2 \times 10^5 \frac{K}{W} \quad (1\text{-}13)$$

Where $L_g$ is the length of glass through which heat conducts (1 mm), $k_g$ is the conductivity of glass (0.81 W/mK), L is the length of the resistor (1000 $\mu$m), w is the width of the resistor (3 $\mu$m), $L_w$ is the length of water through which heat conducts (450 $\mu$m), and $k_w$ is the conductivity of water (0.67 W/mK).

From this it was shown that $R_{glass}$ and $R_{water}$ were the dominant thermal resistances for the system. Thus, heat transfer due to convection in the water and conduction through the platinum were negligible.

An estimate the temperature of the resistor as a function of time for a given current using semi-infinite body theory was then made. For small times (t<1 ms) it was assumed that both the water and glass are semi-infinite bodies with initial temperature $T_a$. At t=0, a constant heat flux (due to the resistor) is applied at the water-glass interface (x=0). The one-dimensional temperature profile was computed using the infinite composite solid solution. The region x>0 is water, x=0 is the resistor, and x<0 is the glass. A one-dimensional model was used for short times since the length of the resistor (L=1000 $\mu$m) was much less than the width of the resistor (L=6 $\mu$m). The temperature was assumed to be constant along the resistor, and lateral conduction was neglected for small times. This model will break down when the lateral conduction becomes significant, and when the assumption of semi-infinite bodies becomes invalid. The boundary conditions for this problem are given below.

$$T_1 = T_2, x=0, t>0 \quad (1\text{-}14)$$

$$\frac{q_1 \alpha_1^{\frac{1}{2}}}{K_1} = \frac{q_2 \alpha_2^{\frac{1}{2}}}{K_2}, x=0, t>o \quad (1\text{-}15)$$

$$q_1 + q_2 = q \quad (1\text{-}16)$$

Where K is the thermal conductivity (0.61 W/mK for water and 0.88 W/mK for glass), q is the heat flux, and the subscript '1' denotes water, and '2' denotes glass.

The solution for the temperature profiles in water and air for a constant heat flux q (W/m$^2$) applied at x=0 is given by Equations (1-17) and (1-18).

$$T_1 - T_o = \frac{2q\sqrt{\alpha_1 \alpha_2 t}}{K_1 \sqrt{\alpha_2} + K_2 \sqrt{\alpha_1}} \, ierfc \frac{x}{2\sqrt{\alpha_1 t}} \quad (1\text{-}17)$$

-continued $$T_2 - T_o = \frac{2q\sqrt{\alpha_1 \alpha_2 t}}{K_1 \sqrt{\alpha_2} + K_2 \sqrt{\alpha_1}} \, ierfc \frac{x}{2\sqrt{\alpha_2 t}} \quad (1\text{-}18)$$

Where $\alpha$ is the thermal diffusivity (1.47$\times 10^{-7}$ m/s$^2$ for water and 4.4$\times 10^{-7}$ m/s$^2$ for glass) and $T_o$ is the initial temperature of the body.

The solution was also used to check the semi-infinite body assumption. For times equal to or less than 1 ms, and a reasonable heat flux such as 2.5$\times 10^{-7}$ W/m$^2$, the heat penetration depths into the glass and water were less than 100 $\mu$m. The total thickness of the water was 450 $\mu$m and of the glass was 1 mm, so the semi-infinite body assumption held true. The one-dimensional model was sufficient for determining the temperature of the resistor at small times.

Using the theory described above, it was possible to predict the power necessary to form a bubble. Since homogeneous bubble nucleation was assumed, the bubbles would form at approximately the superheat limit of water. The value of 305° C. given by the modified Berthelot equation (Table 1) was used. Next, the infinite composite solid solution was used to calculate the temperature of the heater for a given time, say 1 ms. Rearranging equation (1-17) to solve for the heat flux, or power per unit area at position x=0, it was derived:

$$\frac{P}{Lw} = \frac{(K_1 \sqrt{\alpha_2} + K_2 \sqrt{\alpha_1})(T - T_o)}{2\sqrt{\alpha_1 \alpha_2 t}} \quad (1\text{-}19)$$

For an initial temperature of 20° C., and the other properties given above, the heat flux necessary to heat the resistor to 305° C. in 1 ms was computed from (1-19) to be 1.32$\times 10^7$ W/m$^2$. For typical resistor dimensions of w=6 $\mu$m and L=1500 $\mu$m, the necessary power was about 120 mW.

The micromachined wells must be of the proper dimensions to ensure that particles which settle into them remain held in the wells once a flow above them is initiated. The theory of slow viscous flow over cavities has been well characterized and the streamlines for various geometries have been calculated and experimentally verified.

FIG. 9 shows the flow pattern for laminar flow over a rectangular cavity for two different width to height aspect ratios. From these flow patterns it was seen that there was a separating flow line which penetrates slightly into the cavity. Below this line there were one or two vortices, depending on the aspect ratio of the cavities. A particle below the separating flow line would not be swept out of the cavity by a slow flow in the laminar range, though the vortex may agitate the particle.

An order of magnitude calculation was performed in order to compare the relative sizes of the gravity force pulling a particle down, compared to the viscous shear force pulling a particle out of the well. A diagram of a particle in a well with flow over the top is shown in FIG. 10.

The force of gravity acting on the particle was dependent on the difference in density between the particle and the water, $\Delta \rho$. The density of water is approximately 1000 kg/m$^3$, and the density of the polystyrene beads used in the experiments was given by the manufacturer as 1060 kg/m$^3$. The density of cells ranges from 1050–1100 kg/m$^3$. Accordingly, the force of gravity, $F_g$ was computed as shown:

$$F_g = \Delta\rho \frac{4}{3}\pi a^3 g \qquad (1\text{-}20)$$

Where α is the particle radius ($5\times10^{-6}$ m), and g is the gravitational constant.

The viscous shear force acting on the particle was computed by assuming the top of the particle was at the top of the well, and that the flow profile was parabolic. The shear stress at the wall was:

$$\tau_w = \mu \frac{du}{dy}\bigg|_{y=0} \qquad (1\text{-}21)$$

Where $\mu$ is the viscosity of water ($1\times10^{-3}$ kg/ms) and u(y) is the velocity profile as a function of y, the distance from the wall.

Assuming a parabolic velocity profile in the flow chamber, the flow profile was calculated for a known chamber height and volume flow rate.

$$u(y) = \frac{6\bar{V}}{h^2}y(h-y) \qquad (1\text{-}22)$$

$$\bar{V} = \frac{Q}{wh} \qquad (1\text{-}23)$$

$$u(y) = \frac{6Q}{wh^3}y(h-y) \qquad (1\text{-}24)$$

$$\frac{du}{dy}\bigg|_{y=0} = \frac{6Q}{wh^2} \qquad (1\text{-}25)$$

Where $\bar{V}$ is the average flow velocity, w is the chamber width, and h is the chamber height.

The viscous shear force on the cell was estimated as the wall shear stress multiplied by the area being effected, approximately $\pi a^2$.

$$F_v = \tau_w \pi a^2 = \mu \frac{6Q}{wh^2}\pi a^2 \qquad (1\text{-}26)$$

Where α is the cell radius. Finally the ratio of gravity to viscous force was computed.

$$\frac{F_g}{F_v} = \frac{\Delta\rho \frac{4}{3}\pi a^3 g}{\mu \frac{6Q}{wh^2}\pi a^2} = \frac{2\Delta\rho a g w h^2}{9\mu Q} \qquad (1\text{-}27)$$

Using the flow chamber dimensions in FIG. 16, and a range of reasonable flow rates, this ratio was computed.

$$Q = 1\frac{\mu L}{\min}\left(\bar{V} = 2.1\frac{\mu m}{s}\right) \rightarrow \frac{F_g}{F_v} = 292 \qquad (1\text{-}28)$$

$$Q = 10\frac{\mu L}{\min}\left(\bar{V} = 21\frac{\mu m}{s}\right) \rightarrow \frac{F_g}{F_v} = 29 \qquad (1\text{-}29)$$

$$Q = 100\frac{\mu L}{\min}\left(\bar{V} = 210\frac{\mu m}{s}\right) \rightarrow \frac{F_g}{F_v} = 3 \qquad (1\text{-}30)$$

It was necessary that the ratio of forces be greater than one so that the gravity force was stronger than the viscous force. These numbers were used to aid in determining a range of acceptable operating flow rates.

Another relevant piece of information was the time it took for the particles to settle. At low Reynolds number, an isolated rigid spherical particle will settle with its Stokes velocity.

$$U^o = \frac{2a^2(\rho_s - \rho)g}{9\mu} \qquad (1\text{-}31)$$

Where α is the sphere radius (5 $\mu$m for a polystyrene bead), $\rho_s$ is the density of the bead (about 1060 kg/m$^3$), $\rho$ is the density of water (1000 kg/m$^3$), and $\mu$ is the viscosity of water. Using these values a Stokes velocity was calculated as:

$$U^o = 5\times10^{-6}\frac{m}{s} = 5\frac{\mu m}{s} \qquad (1\text{-}32)$$

Using this velocity to check the associated Reynolds number it was found that $$\text{Re} = \frac{\rho U^o a}{\mu} = 3\times10^{-5} \ll 1 \qquad (1\text{-}33)$$

Thus, the assumption of low Reynolds number was valid. The Reynolds number is the ratio of inertial effects to viscous forces. For this case, only the highly viscous regime applied and inertial effects were negligible.

Another value which was checked was the Peclet number. This is the ratio of sedimentation to diffusion. For the particles to settle, the Peclet number must be sufficiently high, otherwise the particles will diffuse throughout the liquid.

$$Pe = \frac{aU^o}{D^o} \qquad (1\text{-}34)$$

$$D^o = \frac{kT}{6\pi\mu a} = 4\times10^{-14}\frac{m^2}{s} \qquad (1\text{-}35)$$

$$Pe = 6\times10^2 \gg 1 \qquad (1\text{-}36)$$

Where $D^o$ is the Brownian diffusivity, and k is the Boltzmann's constant ($1.381\times10^{-16}$ erg/cm). Thus the Peclet number was sufficiently high for settling to dominate over diffusion.

The value calculated above for the Stokes velocity is that for an isolated particle; however, in the case at hand there were many beads settling at once. This was taken into account in the calculation of the hindered velocity. A function of the particle volume fraction is multiplied by the Stokes velocity to result in the hindered velocity of particles in the suspension.

$$U = U^o f(\phi) \qquad (1\text{-}37)$$

$$f(\phi) = (1-\phi)^{5.1} = 0.95 \qquad (1\text{-}38)$$

$$U = 4.75\times10^{-6}\frac{m}{s} = 4.75\frac{\mu m}{s} \qquad (1\text{-}39)$$

Where $\phi$ is the particle volume fraction (about 0.01 for this case). Accordingly, the time necessary for all the particles to settle to the bottom of the flow chamber was calculated using the hindered velocity and the chamber height, the maximum distance to be traveled.

$$t_s = \frac{h}{U} = 166s = 2.76 \text{ min} \qquad (1\text{-}40)$$

Where h is the chamber height (790 μm). This settling time was used as a guideline in experiments.

A more reasonable assumption for calculating the settling time was that the distance the particles fell is an average of half the chamber height. For this case a settling time of about 83 seconds was obtained.

For the given pressure increase associated with the bubble formation in the large sealed well, the flow rate out of the channel in the top of the well was calculated. Since the Reynolds number was in the creeping flow regime (Re<1), inertial effects neglected, and the initial, instantaneous flow out of the channel was computed using the steady state equation for flow through a circular aperture at low Reynolds number.

$$Q = \frac{\Delta P c^3}{3\mu} \qquad (1\text{-}41)$$

Where Q is the volume flow rate, ΔP is the pressure drop, c is the aperture radius (~2.5 or 4 μm), and μ is the water viscosity.

Since the pressure change due to the bubble formation was not easily calculable, the volume flow rate out of the chamber was estimated in a different way. Because water is incompressible, it was assumed in the model that the bubble formation as a volume injection into the chamber resulted in the same volume being ejected from the chamber over the characteristic bubble formation time. For instance, if it took 1 ms to form a 10 μm diameter bubble, then the resulting volume flow rate out of the chamber was calculated as follows.

$$V = \frac{4}{3}\pi r^3 = 5.24 \times 10^{-16} m^3 \qquad (1\text{-}42)$$

$$Q = \frac{V}{t} = 5.24 \times 10^{-13} \frac{m^3}{s} \qquad (1\text{-}43)$$

Using the volume flow rate the average velocity of fluid out of the channel was calculated, and it is seen that the Reynolds number of the flow was indeed low.

$$\overline{V} = \frac{Q}{\pi c^2} = 27 \frac{mm}{s} \qquad (1\text{-}44)$$

$$Re = \frac{\rho \overline{V} c}{\mu} = 0.067 < 1 \qquad (1\text{-}45)$$

Where c is the channel radius (2.5 μm). The force of the fluid jet on the particle was calculated using the Stokes drag force:

$$F_D = 6\pi\mu a \overline{V} = 2.5 \times 10^{-9} N \qquad (1\text{-}46)$$

Where a is the radius of the spherical particle (5 μm for polystyrene beads). Comparing this to the gravitational force (1-20) pulling the particle down, it was found that the force of the jet on the particle was much greater than the force of gravity.

$$F_g = \Delta\rho \frac{4}{3}\pi a^3 g = 3.1 \times 10^{-13} N << F_D \qquad (1\text{-}47)$$

$$\frac{F_D}{F_g} \propto \frac{\overline{V}}{a^2} \qquad (1\text{-}48)$$

Where Δρ is the difference in densities between the water and the polystyrene beads (60 kg/m³). It was seen that as the particle radius increased, the effect of gravity increased. For typical cells, the radius ranges from 5 μm (red blood cells) to 20 μm (most other cells) to 100 μm (embryos and eggs). This device will most likely be used for cells on the order of 5–10 μm in radius so the above calculation was representative of the expected applications.

Design of the Components

A. Resistive Heaters

In order to heat the water to a sufficiently high temperature for microbubble formation, resistive heaters were used. The heaters were made of thin-film platinum on standard glass slides. In designing the heaters it was necessary first to determine a range of resistances and currents to attain the desired power output. The design constraint for this step was the need to keep the current density below the electromigration limit of platinum, while retaining an adequate degree of ohmic heating. The electromigration limit is the maximum current density which platinum can endure before the atoms begin to migrate leaving the resistor inoperable.

The electromigration limit of platinum was reported to be J=9×10⁶ A/cm². It was necessary to design the resistors to operate at a current density below this limit. The resistance of a line heater is calculated as follows.

$$R = \frac{\rho L}{tw} \qquad (1\text{-}49)$$

Where R is the resistance (Ω), L is the length of the resistor (m), t is the film thickness (m), w is the width of the resistor (m), and ρ is resistivity of platinum (Ωm).

The power output of a resistor is a function of the current and resistance, as shown below.

$$P = I^2 R \qquad (1\text{-}50)$$

$$J = \frac{I}{wt} < 9 \times 10^6 \frac{A}{cm^2} \qquad (1\text{-}51)$$

Where I is the current (A) and J is the current density.

Accordingly, as the currents were limited by the electromigration limit, the resistances needed to be sufficiently high to achieve the desired power output. The power output necessary to form a bubble was estimated by using the numbers from Lin et al.'s paper, 'Microbubble Powered Actuator', herein incorporated by reference, where microbubles were formed on a polysilicon line heater. Their resistor was on top of a thin dielectric layer, which was on a silicon wafer. It was reasonable to assume that the heat dissipation of this configuration might well be greater than the heat dissipation of the platinum line resistor fabricated on a glass slide. Also, a liquid with a higher boiling necessary to nucleate bubbles under these conditions was approximately 65 mW.

TABLE 2

Resistor dimensions, resistances, and electromigration limits.

| Slide Name | Resistor | Length (um) | Width (um) | Resistance (Ohms) | Electro-migration Limit (mA) | Max Power (mW) |
|---|---|---|---|---|---|---|
| Slide1 | 1 | 3000 | 3 | 1000 | 22 | 467 |
|  | 2 | 2500 | 3 | 833 | 22 | 389 |
|  | 3 | 500 | 3 | 167 | 22 | 78 |
|  | 4 | 1000 | 3 | 333 | 22 | 156 |
|  | 5 | 1000 | 4 | 250 | 29 | 207 |
|  | 6 | 2000 | 3 | 667 | 22 | 311 |
|  | 7 | 1500 | 3 | 500 | 22 | 233 |
|  | 8 | 1000 | 5 | 200 | 36 | 259 |
| Slide2 | 1 | 3000 | 3,6 | 483 | 22 | 226 |
|  | 2 | 2500 | 3,6 | 400 | 22 | 187 |
|  | 3 | 500 | 3 | 167 | 22 | 78 |
|  | 4 | 1000 | 3,6 | 150 | 22 | 70 |
|  | 5 | 1000 | 6 | 167 | 43 | 311 |
|  | 6 | 2000 | 3,6 | 317 | 22 | 148 |
|  | 7 | 1500 | 3,6 | 233 | 22 | 109 |
|  | 8 | 1000 | 3,5 | 180 | 22 | 84 |
| Slide3 | 1 | 3000 | 6 | 625 | 43 | 1166 |
|  | 2 | 2500 | 6 | 521 | 43 | 972 |
|  | 3 | 500 | 3 | 208 | 22 | 97 |
|  | 4 | 1000 | 3 | 417 | 22 | 194 |
|  | 5 | 1000 | 6 | 208 | 43 | 389 |
|  | 6 | 2000 | 6 | 417 | 43 | 778 |
|  | 7 | 1500 | 6 | 313 | 43 | 583 |
|  | 8 | 1000 | 6 | 208 | 43 | 389 |

Using this as a guideline, the resistances were chosen to range from 167Ω–1000Ω, yielding maximum powers before electromigration of 70–1166 mW. These powers were chosen to be up to an order of magnitude greater than necessary to avoid reaching the electromigration limit in the operation of the resistors.

The resistivity of platinum actually varies with temperature and film deposition conditions, but for these calculations it was taken to be $1 \times 10^{-7}$ Ωm. This is the value for bulk platinum, however the resistivity of thin film platinum can vary widely. Heater widths range from 3–6 $\mu$m and lengths range from 500–3000 $\mu$m. Some heaters were designed to have a narrow region, 100 $\mu$m long in the center, which would be hotter than the rest of the resistor. FIG. 11A is a top view of a heater configuration, while FIG. 11B shows a cross-sectional view of the heater and its dimensions. A table of resistor dimensions, maximum currents, and maximum power outputs is also shown in Table 2.

The lines connecting the contact pads to the heaters were designed to have a far lower resistance than the heaters. This was done to ensure that the lines did not heat up, and that they remained approximately at the ambient temperature. The connector line widths were chosen to be 1500 $\mu$m with lengths of 12 mm. The total resistance of each line was about 7.7Ω.

B. Wells

Square wells were micromachined into silicon in order to hold cells. It was necessary to choose a range of dimensions for these wells to allow for tests with different particle sizes and flow rates. The final goal was to have the ability to trap one particle in each of an array of wells.

TABLE 3

Well Dimensions

| Chip Number | Well Dimension (um) | Hole Dimension (um) |
|---|---|---|
| 1 | 16 | 5 |
| b | 16 | 8 |
| 2 | 10 | 5 |
| 2b | 10 | 8 |
| 3 | 20 | 5 |
| 3b | 20 | 8 |
| 4 | 30 | 5 |
| 4b | 30 | 8 |
| 5 | 40 | 5 |
| 5b | 40 | 8 |
| 6 | 50 | 5 |
| 6b | 50 | 8 |

Side lengths of the wells were chosen to range from 10 $\mu$m, corresponding to the smallest test bead size, up to 50 $\mu$m. Well sizes ranging from 10–50 $\mu$m were chosen. Narrow channel widths of 5 $\mu$m and 8 $\mu$m were chosen since both these sizes are smaller than the minimum test particle size of 10 $\mu$m and it is necessary that particles not be able to settle down into the narrow channel. The table of well dimensions is shown in Table 3. A diagram of the well geometry is shown in FIG. 12A, which shows a side view, while FIG. 12B shows a top-down view.

Figure 13A:
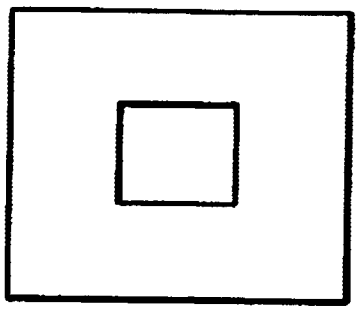
FIGS. 13A, 13B, and 13C shows a top-down view of a silicon processing mask set for use in the present invention.
Figure 13B:
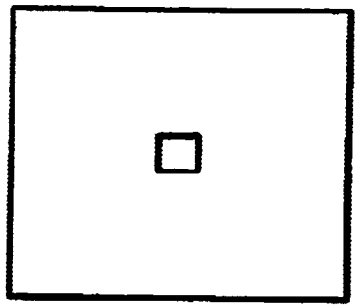
Figure 13C:
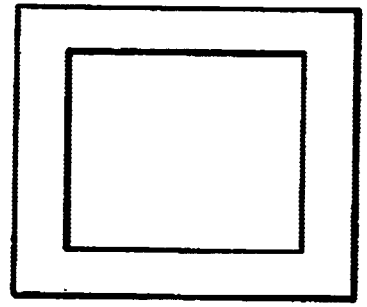
Figure 14A:
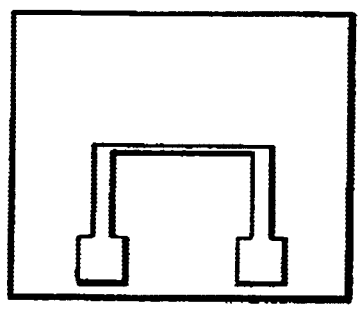
FIG. 14 shows a top-down view of a glass processing mask.

Photomasks for use in the device fabrication were created using standard mask layout software. The mask set for the silicon processing are shown in FIGS. 13A–13C and the glass mask set is shown in FIG. 14A and 14B.

Three masks were designed for the silicon portion of the device processing. One mask was created for the cell wells (FIG. 13A), one for the narrow channels within the wells (FIG. 13B), and one for the large wells (FIG. 13C) etched from the backside of the wafer to enclose the heaters. Two masks were made for the fabrication of the platinum heaters on the glass slides. One mask (FIG. 14) was designed to pattern the metal.

Figure 15:
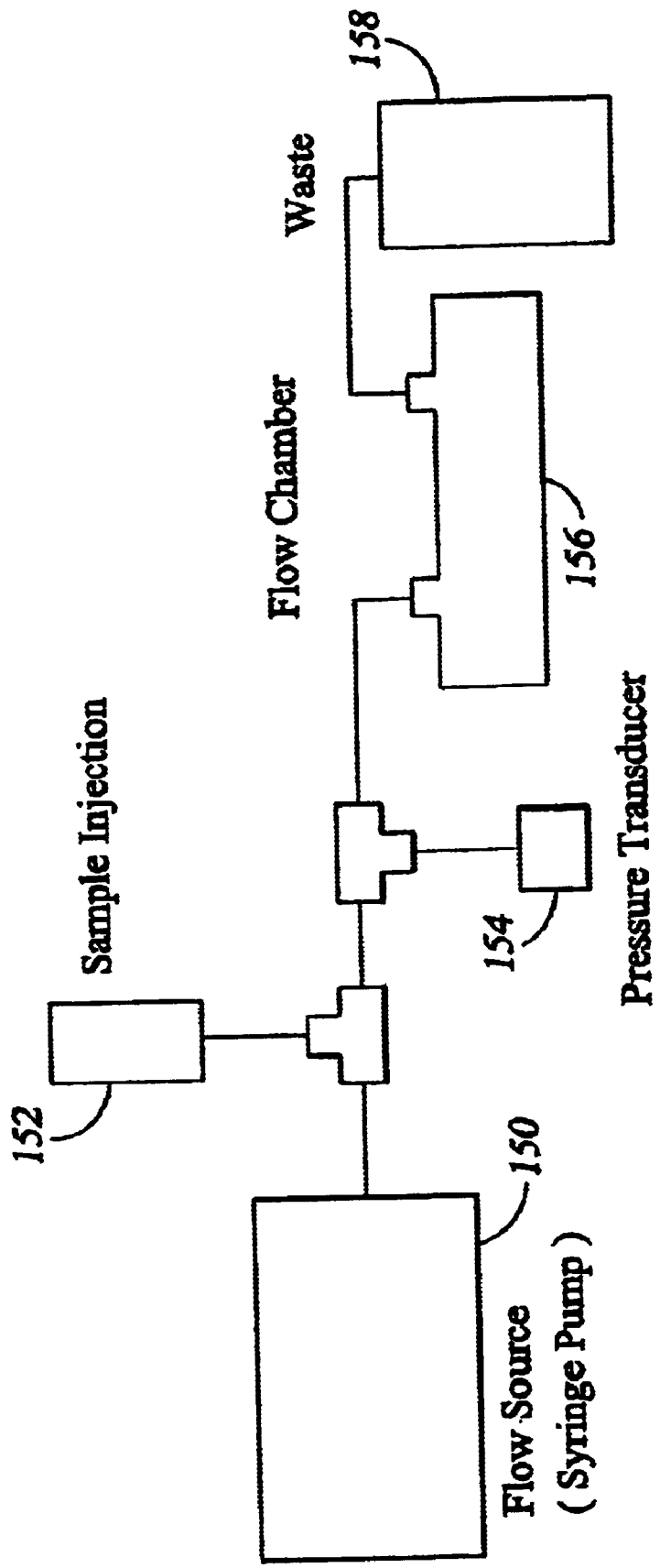
FIG. 15 shows a diagram of a flow system for testing devices of the present invention.

In order to test the finished devices, a fluidic system as illustrated in FIG. 15 was designed and assembled. A syringe pump 150 was used as the flow source for the bulk fluid, and flow rates ranging from 1 to 100 $\mu$L/min were specified. Beads, cells, or cell stimuli were injected through the sample injection valve 152. A pressure sensor 154 was located before the flow chamber 156 so that the pressure drop across the chamber could be monitored. All fluid was outlet into a waste beaker 158 which could be reused if desired.

Figure 16A:
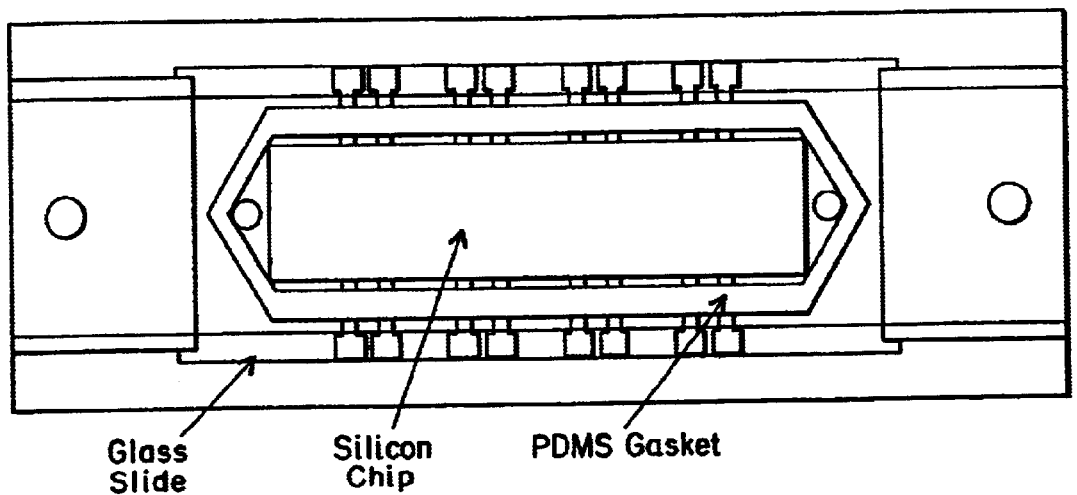
FIG. 16A shows a top-down view of a flow chamber of the present invention.
Figure 16B:
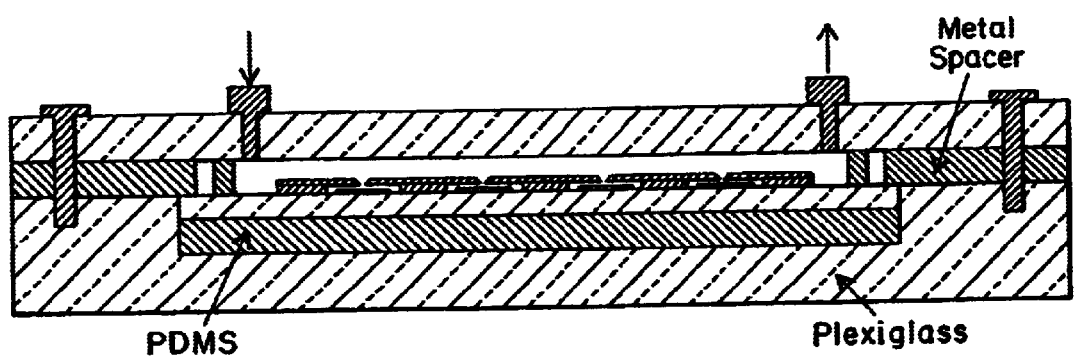
FIG. 16B shows a side view of the flow chamber of FIG. 16A.

A schematic of the flow chamber 156 is shown in FIGS. 16A and 16B. The flow chamber was machined from plexiglass so that it was clear and a microscope was used to observe cell behavior from above the chamber. HPLC (high-performance liquid chromatography) fittings were used with tube dimensions of 1/16 inch outer diameter and 0.020 inch inner diameter. The gasket between the slide and the top cover were made from PDMS (poly dimethyl siloxane), a flexible polymer. A seal was formed by screwing the top plate down onto the bottom plate. Aluminum molds were machined in order to create PDMS gaskets of the proper dimensions. Gaskets were compressed until a hard stop was reached. The stop was provided by the spacers, made of metal shim stock, in order to accurately specify the channel height. The aspect ratio of the channel's width to height was greater than 10, allowing the assumption of a parabolic velocity profile-plane Poiseuille flow.

The height of the flow chamber was 790 $\mu$m (determined by thickness of metal spacer). Flow rates ranged from 1 to 100 $\mu$L/min and corresponded to Reynolds numbers of 0.001–0.1. In this creeping flow regime, the entrance length for fully developed flow was calculated to be negligible.

These calculations are shown below.

$$\overline{V}_{min} = \frac{Q_{min}}{A_c} = 1.77 \frac{\mu m}{s} \qquad (1-52)$$

$$\overline{V}_{max} = \frac{Q_{max}}{A_c} = 177 \frac{\mu m}{s} \qquad (1-53)$$

$$Re_{min} = \frac{h\overline{V}_{min}}{v} = 0.0011 \qquad (1-54)$$

$$Re_{max} = \frac{h\overline{V}_{max}}{v} = 0.11 \qquad (1-55)$$

$$X_e \approx \frac{h\,Re_{max}}{30} = 2.6\mu m \qquad (1-56)$$

Where $\overline{V}_{min}$ is the minimum average velocity, $Q_{min}$ is the minimum volume flow rate (1 $\mu$L/min), $A_c$ is the cross-sectional area of the channel (h=790 $\mu$m, w=12 mm), $\overline{V}_{min}$ is the maximum average velocity, $Q_{max}$ is the maximum volume flow rate (100 $\mu$L/min), Re is the Reynolds number, v is the kinematic viscosity of water (1×10$^{-6}$ m$^2$/s), and $X_e$ is the entrance length for fully developed flow.

Electrical connections to the contact pads were made using a probe station. Contact pads were positioned outside of the PDMS gasket and were thus kept outside of the fluid flow.

In order to ensure the proper flow characteristics of the flow chamber, dye was injected into the flow and the resulting profile was observed. The results were used to discover problems such as blockages in the flow chamber and correct them. When a uniform flow was established, 10 $\mu$m diameter beads were injected into the flow and observed under a microscope.

The pressure drop across the flow chamber was monitored using a pressure transducer. The majority of the pressure drop was caused by the connector tubing, but by comparing the pressure reading to the theoretical value, the presence of bubbles and other blockages to the flow may be detected.

Figure 17:
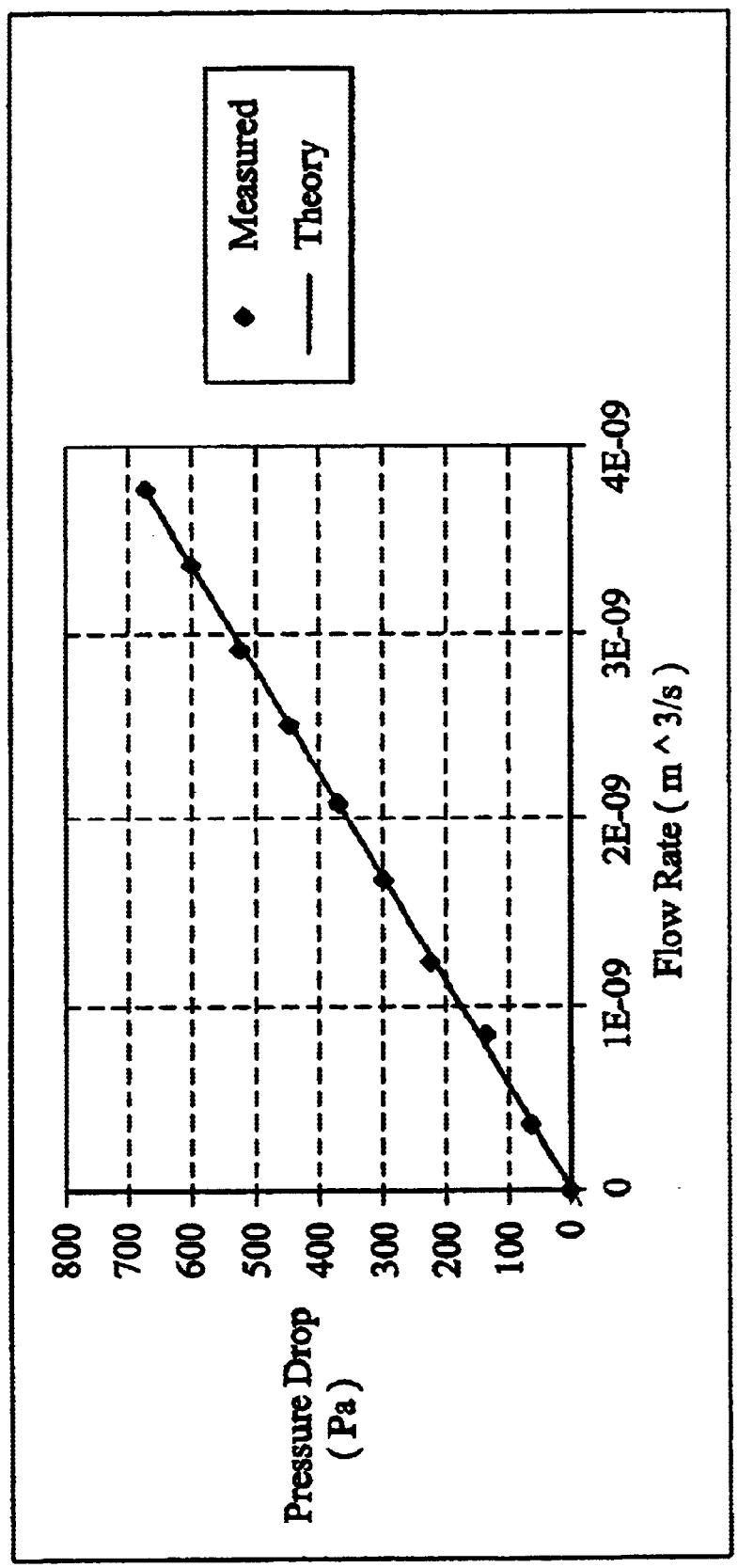
FIG. 17 is a graph of pressure drop vs. flow rate for the flow chamber of FIGS. 16A and 16B.

The pressure versus flow rate plot for the flow chamber is shown in FIG. 17. The theoretical value is plotted with the experimental measurements. When these two values do not match, a blockage in the chamber or tubing is probable.

The pressure drop through the tubing was calculated using the following equation.

$$\Delta P = \frac{-8\mu Q}{\pi r^4} \Delta x \qquad (1-57)$$

Where $\mu$ is the viscosity of water (1×10$^{-3}$ kg/ms), r is the tube radius (0.254 mm), and $\Delta x$ is the tube length (m). The pressure drop through the chamber was calculated to be negligible in comparison. The flow chamber schematic with dimensions is shown in FIGS. 18A–18D.

Fabrication of the Components

The platinum heaters were fabricated on standard 1×3 in glass slides using a lift-off process. The process flow is shown in FIGS. 19A–19C. In the first step illustrated as FIG. 19A, photoresist was spun onto the glass slide, exposed using mask 4, and developed. Next, 100 Å of titanium and 1000 Å of platinum were evaporated onto the slide, as seen in FIG. 19B. The titanium served as an adhesion layer between the glass and the platinum. In the following step, the slide was submerged in acetone to dissolve the photoresist and lift away the metal which was deposited on top of the photoresist, as depicted in FIG. 19C. Only the platinum resistors were left on the glass slide. Some slides were then annealed in a tube furnace at 600° C. for 1 hour. While not used in this example, it is contemplated that photoresist may be applied manually to the slide to attach the silicon chip to the slide.

The silicon chip process flow is shown in FIGS. 20A–20H. Double Side Polished (DSP) four inch diameter silicon wafers were used. In the first step shown as FIG. 20A, 1 $\mu$m of thermal oxide was grown on the wafer. Next the oxide was patterned using mask 1, FIG. 20B. Resist was spun on top of the oxide and patterned using mask 2. The resulting configuration was called a nested mask, shown as FIG. 20C.

First the photoresist mask was used to etch the narrow 5 $\mu$m trenches, then the oxide mask was used to etch the cell wells, as shown in FIGS. 20D and 20E. Next the wafer was turned over and photoresist was deposited and patterned on the back side using mask 3 (FIG. 20F). A deep silicon etch was then performed to etch through the wafer and intersect the narrow trenches etched previously (FIG. 20G) to obtain a finished wafer (FIG. 20H).

Figure 21B:
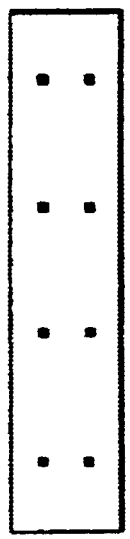
FIGS. 21A–21D show a process of assembling the silicon wafer of FIGS. 20A–20H onto the glass slide of FIGS. 19A–19C.
Figure 21D:
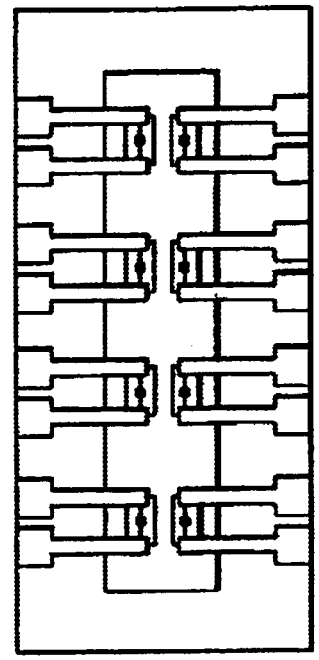
Figure 21A:
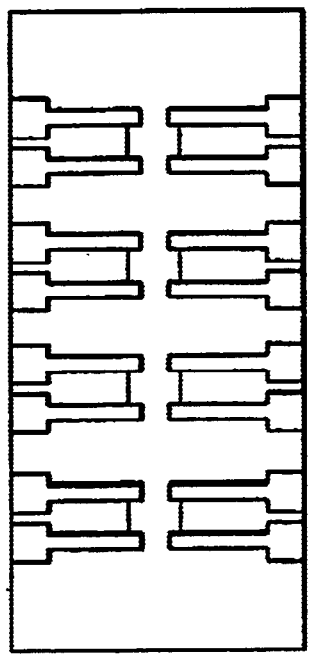
Figure 21C:
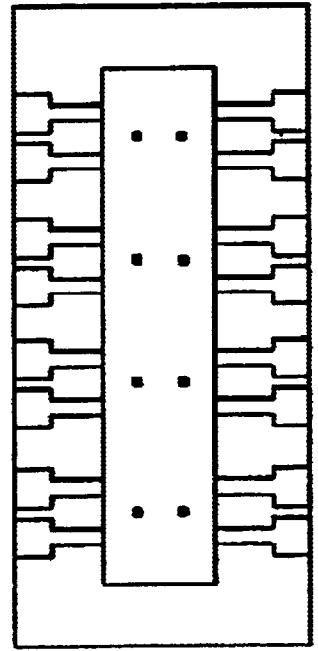

A complete device consisted of a silicon chip attached to a glass slide by photoresist, as shown in FIGS. 21C and D. The resist provided a water-tight seal so that volume expansion in the bubble wells resulted in a burst of fluid being pushed through the narrow channel and ejecting a cell.

To facilitate the assembly process, alignment marks were fabricated on the glass slide and matching holes were etched in the silicon chip. The alignment tolerances were sufficiently large (about 2 mm) that the chip could be aligned to the slide by hand using just the naked eye, while still positioning the bubble wells over the platinum heaters.

Photoresist was painted onto the silicon chip around the bubble wells using a toothpick. Drops of water were deposited into each well using a pipette, then the glass slide was visually aligned from above and stuck down onto the chip. The drops of water served to fill the bubble wells and get pushed through the narrow channel to fill it with water. The device was now ready to be tested in the flow chamber.

Next, the resistance of the platinum resistors were studied. The film thickness was first measured using a profilometer. The platinum thickness measurements ranged from about 800–900 Å, so the average value of 850 Å was used in the subsequent calculations. The resistance along metal lines wide enough not to be strongly affected by variation of a few microns was measured using a multimeter. The lines used for this measurement were measured in an optical microscope to be about 1510 $\mu$m wide. The length of the lines was about 8 mm. Knowing the width, thickness, and length of these lines, as well as the measured resistance, the resistivity of the thin film platinum at room temperature was determined. The measured resistance was 15 $\Omega$, and the computed resistivity was calculated below.

$$\rho = \frac{twR}{L} = 2.4 \times 10^{-7} \Omega m \qquad (1-58)$$

Where t is the film thickness (850 Å), w is the line width (1513 $\mu$m) R is the measured resistance (15 $\Omega$), and L is the length of the line (8 mm). This resistivity was more than twice the value for bulk platinum 1×10$^{-7}$ $\Omega$m), but was a reasonable value for thin film platinum. This is because bulk platinum is a crystalline material, whereas thin film platinum is polycrystalline and the grain boundaries significantly increase resistance.

Next, the resistance of the resistors was measured with a multimeter. Using the value of resistivity from above, the line width of each resistor was determined. The line widths were also measured using an optical microscope to an accuracy of about ±1 μm. The results of this measurement for two different resistor slides are shown in Table 4.

TABLE 4

Resistance measurements and calculated, measured, and designed line widths.

| | Resistor # | L (um) | R (Ohms) | Computed Line Width (um) | Measured (um) | Design (um) |
|---|---|---|---|---|---|---|
| Slide 1 | 1 | 3000 | 1020 | 8.34 | 8 | 3 |
| | 2 | 2500 | 845 | 8.39 | 8 | 3 |
| | 3 | 500 | 185 | 7.66 | 8 | 3 |
| | 4 | 1000 | 347 | 8.17 | 8 | 3 |
| | 5 | 1000 | 272 | 10.42 | 10 | 4 |
| | 6 | 2000 | 672 | 8.44 | 9 | 3 |
| | 7 | 1500 | 504 | 8.44 | 8 | 3 |
| | 8 | 1000 | 260 | 10.90 | 10 | 5 |
| Slide 3 | 1 | 3000 | 850 | 10.01 | 10 | 6 |
| | 2 | 2500 | 728 | 9.74 | 10 | 6 |
| | 3 | 500 | 247 | 5.74 | 6 | 3 |
| | 4 | 1000 | 479 | 5.92 | 6 | 3 |
| | 5 | 1000 | 316 | 8.97 | 9 | 6 |
| | 6 | 2000 | 620 | 9.15 | 9 | 6 |
| | 7 | 1500 | 450 | 9.45 | 10 | 6 |
| | 8 | 1000 | 270 | 10.50 | 10 | 6 |

Figure 22:
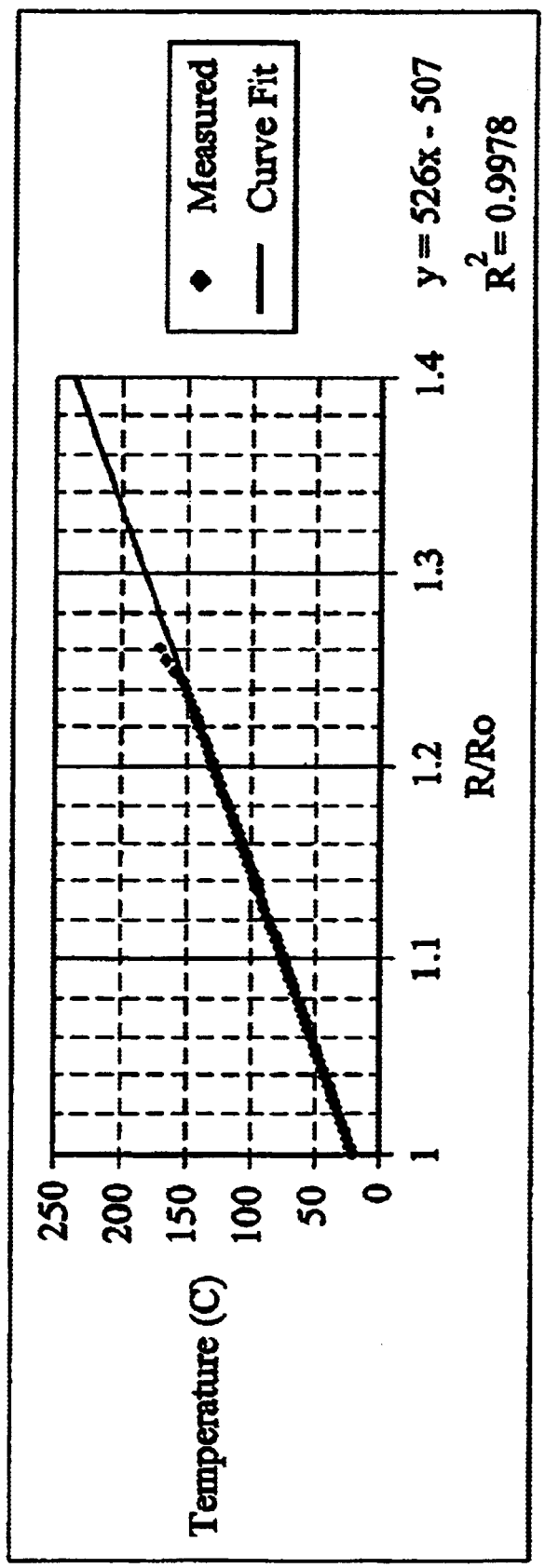
FIG. 22 is a graph of temperature v. resistance for platinum resistors of the present invention.

From this it was determined that the measured and calculated line widths were within the range of error for the measurements, confirming the resistivity calculation. The resulting plot of normalized resistance versus temperature is shown in FIG. 22. The resistance was normalized using the resistance at room temperature. This curve was used later to predict the temperature of a resistor, knowing the resistance at room temperature and measuring the resistance during operation.

Using the cross-sectional area of the resistors, the maximum current before electromigration was calculated. It was known that maximum current density before electromigration is $9 \times 10^6$ A/cm$^2$. Using this the maximum current for each resistor was calcualted. The results of this are shown in Table 5.

TABLE 5

Computed electromigration limits for resistors.

| | Resistor # | Computed Line Width (um) | Maximum Current (mA) |
|---|---|---|---|
| Slide 1 | 1 | 8.3 | 71.3 |
| | 2 | 8.4 | 71.7 |
| | 3 | 7.7 | 65.5 |
| | 4 | 8.2 | 69.9 |
| | 5 | 10.4 | 89.1 |
| | 6 | 8.4 | 72.1 |
| | 7 | 8.4 | 72.1 |
| | 8 | 10.9 | 93.2 |
| Slide 3 | 1 | 10.0 | 85.6 |
| | 2 | 9.7 | 83.2 |
| | 3 | 5.7 | 49.1 |
| | 4 | 5.9 | 50.6 |
| | 5 | 9.0 | 76.7 |
| | 6 | 9.1 | 78.2 |
| | 7 | 9.5 | 80.8 |
| | 8 | 10.5 | 89.8 |

These results were used as guidelines during testing of microbubble devices to avoid burning out the resistors.

Figure 23:
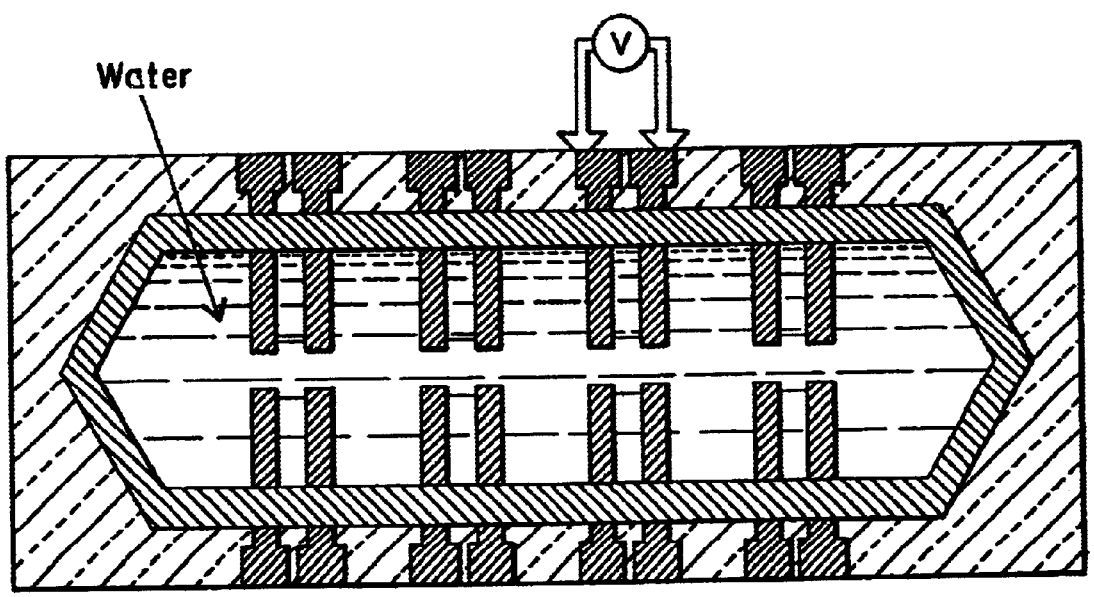
FIG. 23 shows a configuration for a resistor testing apparatus used in the present invention.

The main objective for the resistors was that they be able to reach high enough temperatures to boil water. The resis- tors were tested on a probe station using an HP4145b to vary the voltage and measure the resulting current through the resistor. A PDMS gasket was placed on top of the slide and filled with water. The gasket contained the water and kept it from touching the electrical contacts and probes. FIG. 23 is a schematic of this configuration.

Upon ramping the voltage across resistors from zero to about 20–30 V, there was violent bubbling originating not from the hot part of the resistor, but from the edges of the wide connector lines. It was evident that the bubbles were gas bubbles and not water vapor bubbles because the bubbles did not condense when the heater was turned off. Further experimentation revealed that electrolysis of the water was occurring and the water was being broken down into hydrogen and oxygen. After flushing the slides, gaskets, and glassware for several minutes with deionized water, and testing again, the problem of electrolysis was eliminated.

Figure 24:
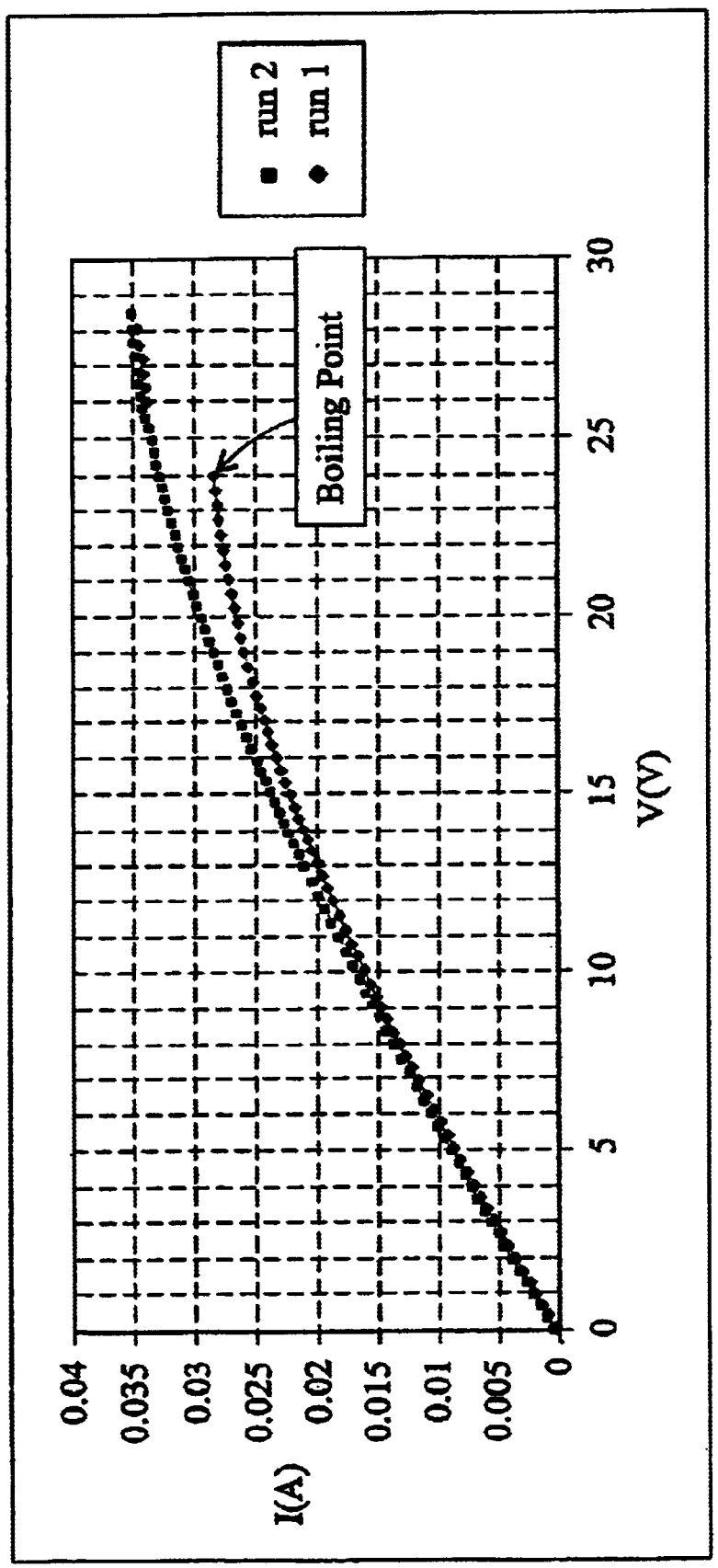
FIG. 24 is a graph of current v. voltage for the onset of boiling in platinum line resistors of the present invention.

When the problem of electrolysis was eliminated, the resistors were once again tested in water. When the resistor reached a sufficient temperature, boiling occurred along the length of the heater. After the power was turned off, small air bubbles remained on the resistor due to the dissolved gas coming out of solution, as described previously. In subsequent tests, the air bubbles served as nucleation sites for boiling, the inception of boiling occurred at a much lower temperature. When boiling begins and bubbles form on the resistor, the heat dissipation into the water increases drastically. This is a favorable phenomenon for the operation of the device because the onset of boiling is represented as a sharp increase in current on the I-V curve. This is because when the heat dissipation increases, the temperature decreases, resulting in a lower resistance and thus a higher current through the resistor. An I-V curve for the onset of boiling on a line resistor is shown in FIG. 24.

In this I-V curve it is shown that for the first run when no bubbles were present on the line, there is a sharp jump in current at the onset of boiling. For the second run, residual bubbles were left on the heater and served as nucleation sites for boiling resulting in a smooth I-V curve with boiling beginning at a lower temperature. The two curves are very close after the boiling begins for run 1.

In later tests, when no dissolved gas came out of solution, the jump in the I-V curve occurred during each heating cycle for the resistors, since there were no residual air bubbles left when the power was turned off.

Figure 25:
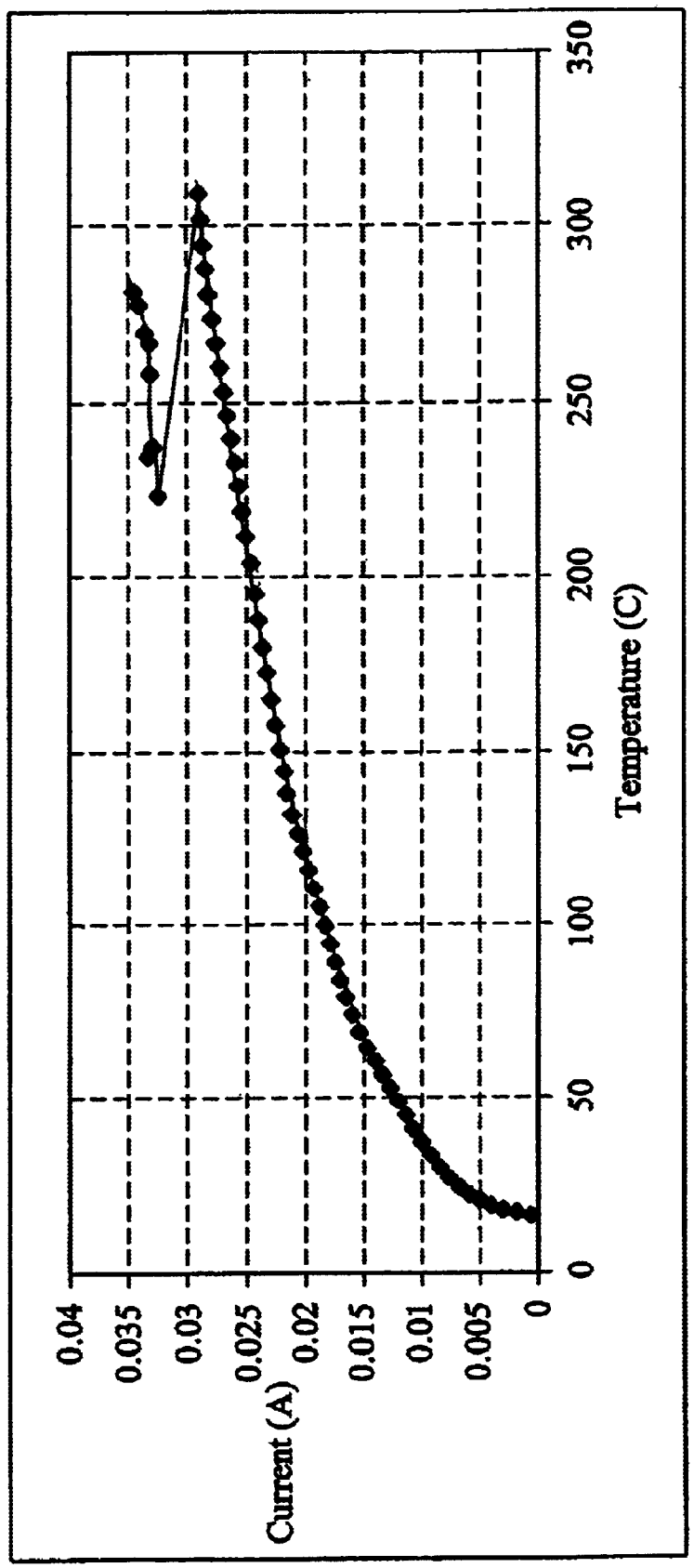
FIG. 25 is a graph of current v. temperature for the platinum line resistors of FIG. 24.

Using the calibration given in FIG. 22 for the temperature-resistance relationship of the resistor, the temperature of the resistor for each current was plotted to find the boiling temperature. The current vs. temperature plot corresponding to the I-V curve shown above is in FIG. 25. On this plot water is shown to boil at approximately 308° C., at which point the temperature drops rapidly due to the increased convective heat transfer associated with boiling.

The boiling points for the 5 resistors tested ranged from 250° C. to 308° C. The lowest calculated value for the superheat limit of water was found to be 273° C., so these measured boiling points suggest that the bubble nucleation occurs either in the homogeneous regime, or by a weak heterogeneous mechanism.

Figure 26:
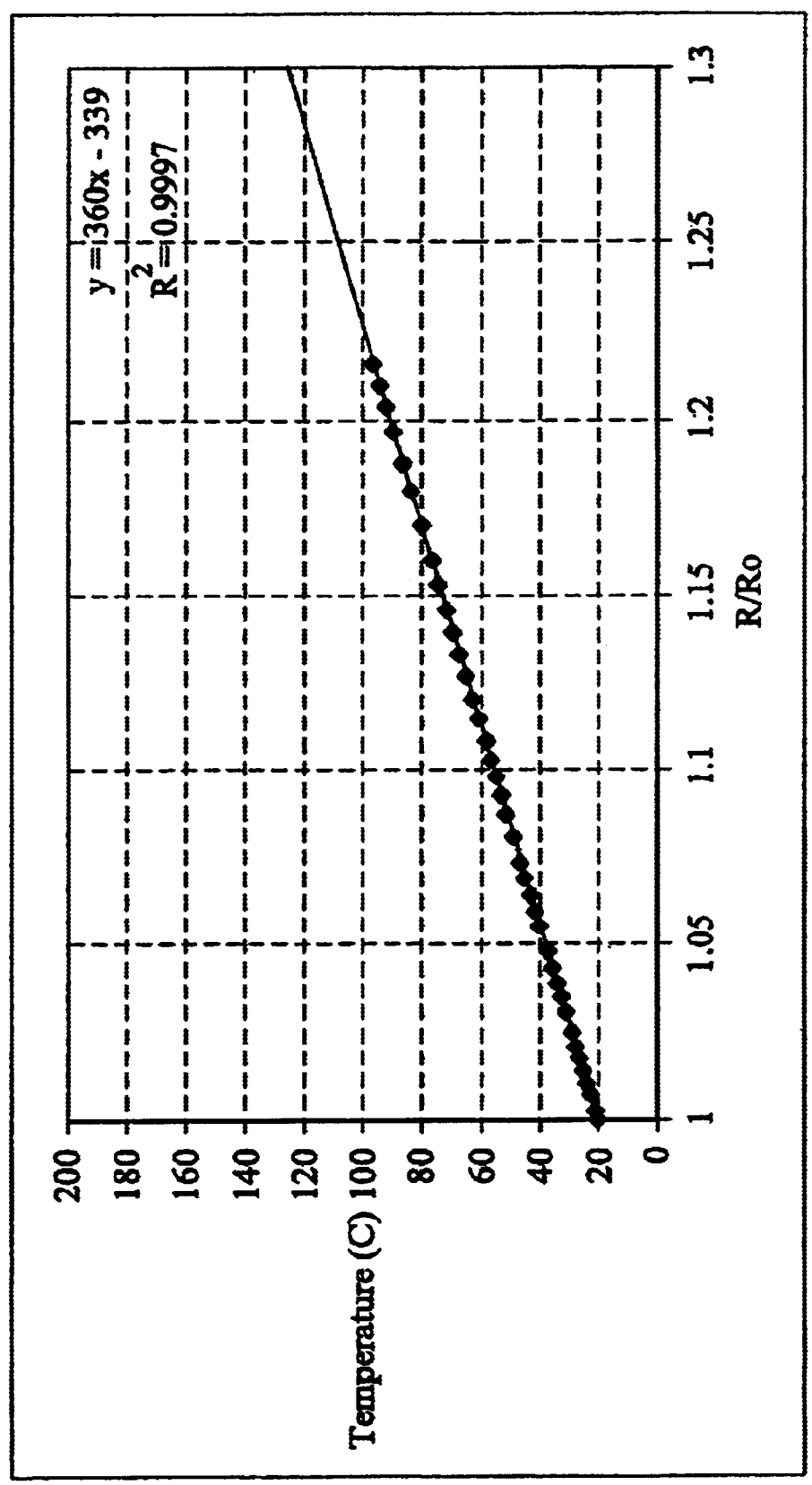
FIG. 26 is a graph of temperature v. resistance for a set of annealed platinum line resistors of the present invention.

After a considerable amount of testing of the resistors characterized above, a drift in the boiling temperature became apparent. In order to determine the reason for this, the resistors were recalibrated as described in the previous section. The temperature versus normalized resistance curve is shown in FIG. 26. The dramatic change in temperature-resistance characterization led to the testing of a second generation of resistors. It is thought that these changed characteristics are caused over time by the heating of the resistors. The operation of the resistors effectively caused them to anneal themselves. Annealing changed the geography of the platinum grain boundaries and thus changed the resistivity of the resistors.

In order to avoid this effect in future testing, new resistor slides were annealed at 600° C. for 1 hour as the last step in their process. This temperature is higher than operating temperatures are likely to reach, but not so high that major agglomeration will result. Once the anneal was complete, the new resistors were characterized as described above for the first generation resistors.

First, the resistivity of the platinum at room temperature was found to be $2.056 \times 10^{-7}$ $\Omega$m, less than the unannealed resistors that were $2.41 \times 10^{-7}$ $\Omega$m. Next the resistances were measured using a multimeter, and the line widths were computed as before, as shown in Table 6.

TABLE 6

Measured resistances and computed line widths of second generation resistors.

| | Resistor # | L (um) | R (Ohms) | Computed Line Width (um) | Design (um) |
|---|---|---|---|---|---|
| Slide 3 | 1 | 3000 | 553 | 13.12 | 6 |
| | 2 | 2500 | 481 | 12.57 | 6 |
| | 3 | 500 | 146 | 8.28 | 3 |
| | 4 | 1000 | 281 | 8.61 | 3 |
| | 5 | 1000 | 205 | 11.80 | 6 |
| | 6 | 2000 | 409 | 11.83 | 6 |
| | 7 | 1500 | 310 | 11.70 | 6 |
| | 8 | 1000 | 186 | 13.00 | 6 |

Figure 27:
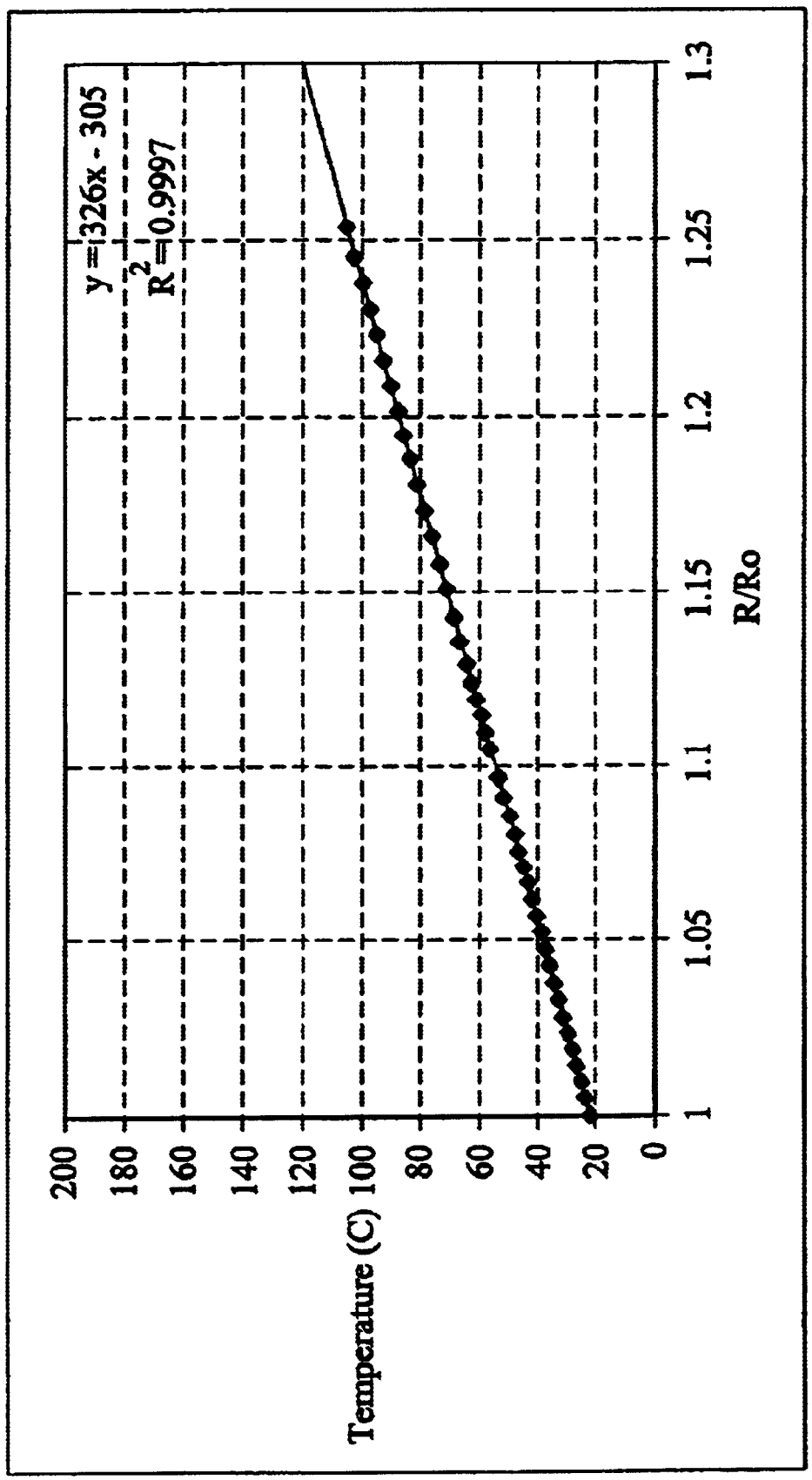
FIG. 27 is a graph of temperature v. resistance for a set of annealed platinum line resistors which were heated on a hot plate.

The temperature-resistance characteristic or the resistors was then measured on a hotplate as described above, and is shown in FIG. 27.

At this point, the bubble formation characteristics of the resistors were tested as described previously with boiled, deionized water. Voltages were ramped up by 0.5 V steps with delay times of 1 ms using the HP4145b, as before. None of these tests resulted in residual gas bubbles since the delay time was short, and the maximum voltage used was just above the bubble nucleation voltage, determined by testing. All resulting vapor bubbles condensed back into the liquid phase within one minute of stop of current flow.

Figure 28:
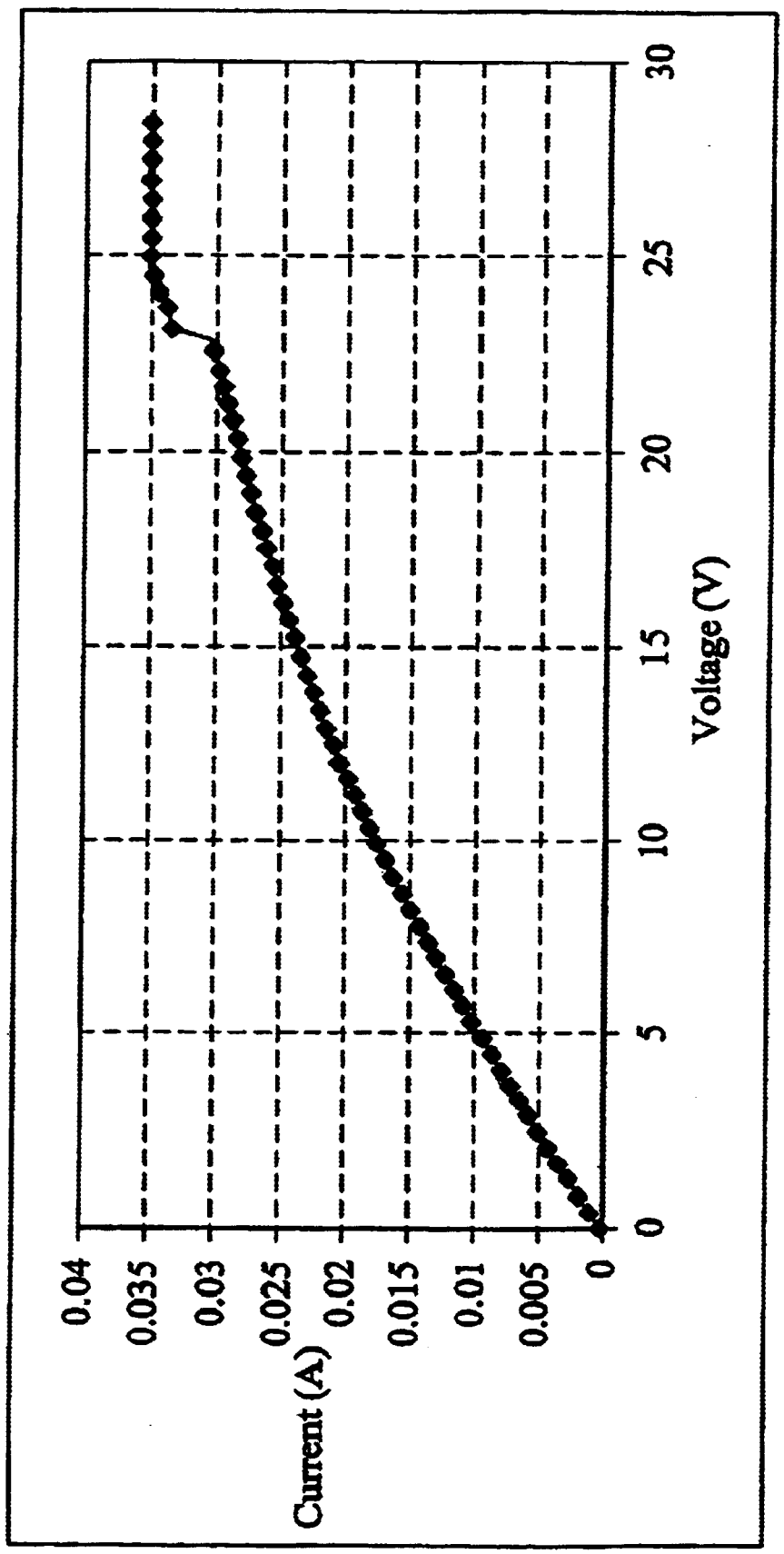
FIG. 28 is a graph of current v. voltage for a set of annealed platinum line resistors of the present invention.
Figure 29:
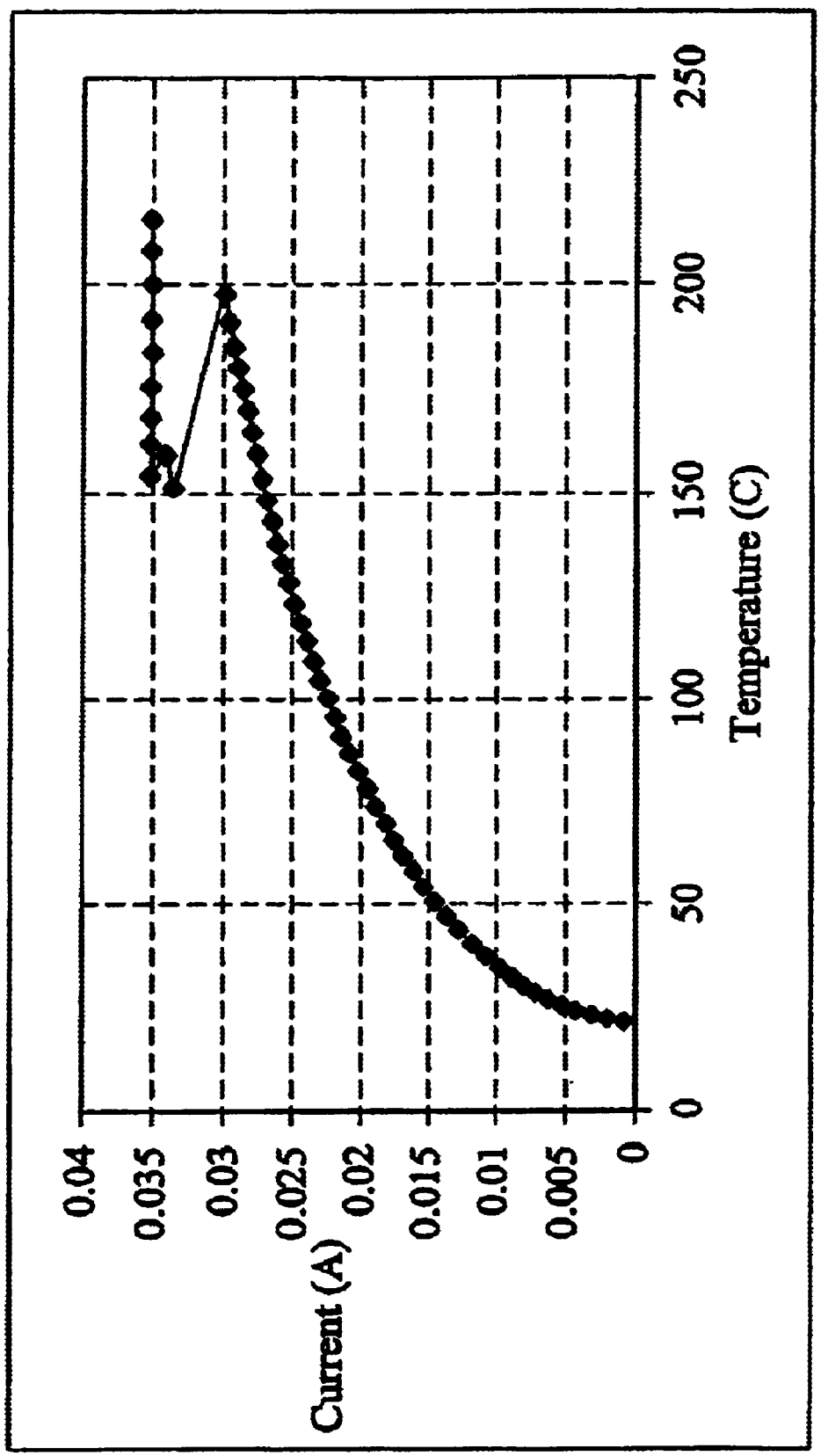
FIG. 29 is a graph of current v. temperature for the resistors of FIG. 28.

A resulting I-V curve is shown in FIG. 28, and the corresponding temperature curve is shown in FIG. 29. From the curve we can see that the onset of boiling occurred at about 200° C., a much lower temperature than for the first generation resistors, and well below the superheat limit of water. For the 8 second generation resistors tested, boiling points ranged from 128° C.–200° C., with the majority of the temperatures above 180° C. This suggests that the boiling is in the heterogeneous nucleation regime as discussed earlier. The cavity radii corresponding to these boiling inception temperatures are calculated from Equation (1-59).

$$r_c = \frac{2\sigma T_{sat}}{h_{fg}\rho_v(T_w - T_{sat})} \quad (1\text{-}59)$$

The results of this calculation are shown in Table 7.

TABLE 7

Bubble nucleation cavity radii corresponding to measured boiling temperatures.

| Resistor # | Boiling Temperature (C) | Cavity Radius (um) |
|---|---|---|
| 1 | 200.7 | 0.33 |
| 2 | 198.3 | 0.34 |
| 3 | 170.4 | 0.47 |
| 4 | 183.2 | 0.40 |
| 5 | 128 | 1.19 |
| 6 | 188 | 0.38 |
| 7 | 189 | 0.37 |
| 8 | 169 | 0.48 |

From this we can see that bubbles were nucleated in radii ranging from 0.3–1.2 $\mu$m. As discussed previously, these cavities were most likely formed during the 600° C. anneal, during which the grooves at the grain boundaries widened creating cavities.

Figure 30:
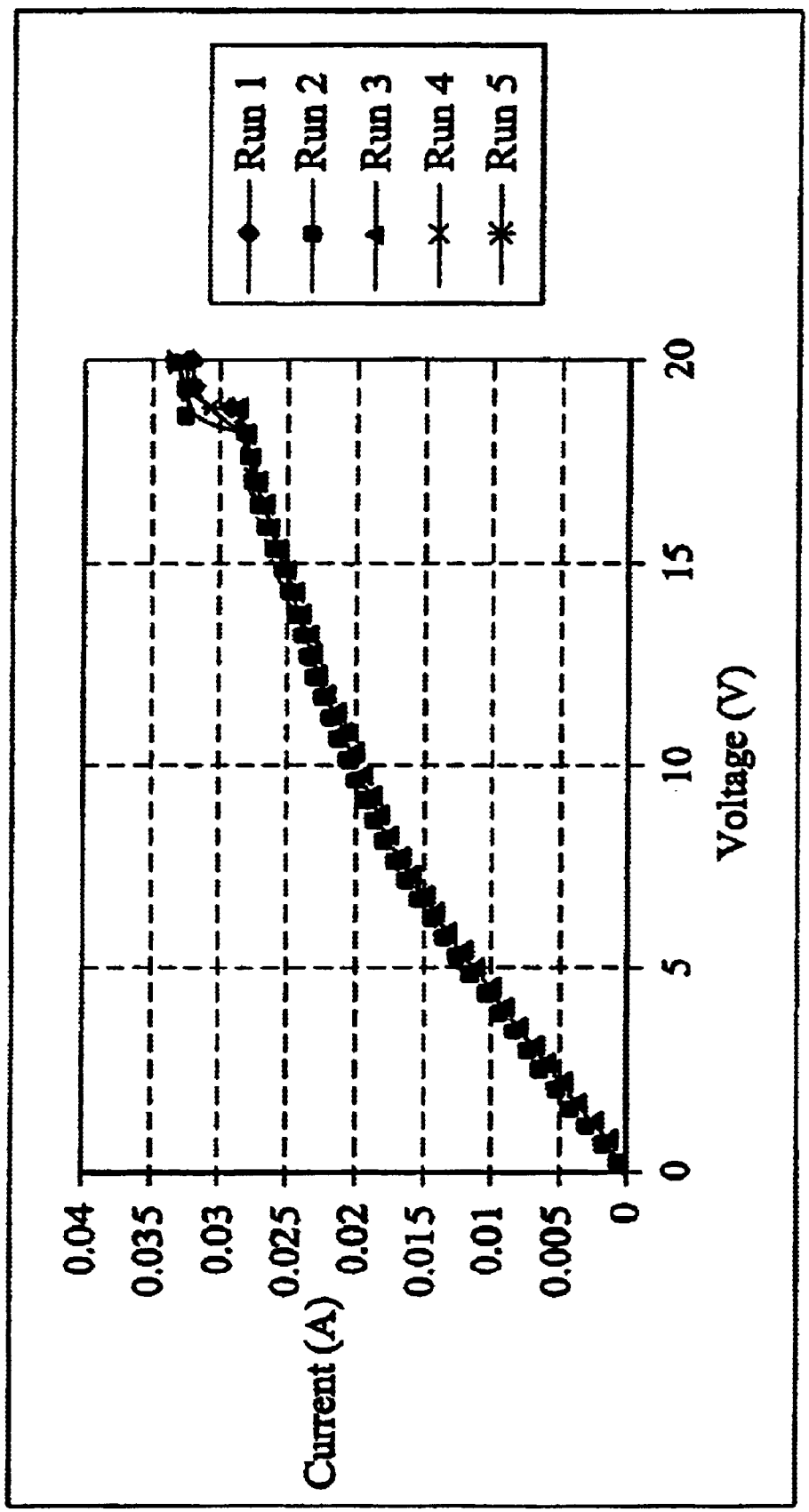
FIG. 30 is a graph of current v. voltage for the resistors of FIG. 28 under repeated boiling tests.

The second generation resistors were also tested for the repeatability of their boiling temperatures. I-V curves were measured as in the previous section, and then remeasured for the same conditions several times. Between measurements, time was given for the vapor bubbles to dissipate so that the characteristic jump in the I-V curve at boiling could be observed with each measurement. The boiling point was found to be very repeatable, and an example of the results is shown in FIG. 30. This result demonstrated the potential of a control system based on a jump in the I-V curve at the onset of boiling, since the boiling point remained fixed.

Another interesting result from this testing is that for a particular resistor, the bubbles tended to nucleate in the same locations on the resistor each time. This strengthens the hypothesis that the bubbles are nucleating in the heterogeneous regime, in cavities created by thermal grooving caused by the annealing.

Results

The cell chip was attached to the glass resistor slide as described earlier, and then tested in two ways. First tests were done with stagnant fluid on the device. Then the device was put into the flow chamber for testing. The results of these tests are described below.

For these tests, several drops of bulk solution were placed on top of the cell chip, and contained by the PDMS gasket. A drop of the polystyrene bead solution was then added to the bulk fluid and allowed to settle. The bulk solution was a 0.05% solution of Triton x-100 surfactant in deionized water. The bead solution was about 1% beads diluted in the same bulk solution. Some of the beads settled into wells, as shown in FIG. 42. When voltage across the resistor was ramped up by the HP4145b, an I-V curve with a jump similar to that in FIG. 24 was produced, demonstrating that boiling had occurred. Consequently, the bubble formation under the well caused a volume expansion which rapidly ejected the beads from the well. First the beads are in the well, and then they are rapidly expelled. This sequence was also captured on videotape, and the process was repeated multiple times with the same success.

Preliminary dynamic testing was performed in the flow chamber. Beads were ejected in a similar way to the static test, and carried away in the flow. The preliminary tests suggested that the beads are held in the wells against a reasonable flow rate, and are ejected into the flow when a microbubble forms.

While the invention has been particularly shown and described above with reference to several preferred embodiments and variations thereon, it is to be understood that additional variations could be made in the invention by those skilled in the art while still remaining within the spirit and scope of the invention, and that the invention is intended to include any such variations, being limited only by the scope of the appended claims.

What is claimed is:

1. A cell sorting apparatus for manipulation of cells comprising:
an array of geometric sites arranged across a substrate in a defined pattern, each site being dimensioned and configured to hold a single cell, wherein each site includes a capture mechanism comprising a well that is capable of selectively capturing the single cell, and further wherein each site includes a release mechanism comprising an actuator disposed within a chamber attached to the well for selectively releasing the single cell from the site.

2. The apparatus of claim 1, wherein each site has a unique address and is independently controllable with respect to another site.

3. The apparatus of claim 1, wherein each well is sized and shaped to hold only the single cell.

4. The apparatus of claim 1, wherein the well has an inner diameter ranging from about 10 to 50 microns.

5. The apparatus of claim 1, wherein each well is connected by a narrow channel to the chamber.

6. The apparatus of claim 5, wherein the narrow channel has a width of about 5 to 8 microns.

7. The apparatus of claim 1, wherein the actuator comprises a heating element.

8. The apparatus of claim 7, wherein the heating element is configured to induces bubble nucleation sufficient to create a volume expansion within the chamber to eject the cell out of the well.

9. The apparatus of claim 8, wherein the heating element comprises two wide low-resistance lines connected by a high-impedance line resistor.

10. The apparatus of claim 8, wherein the wide low-resistance lines are about 12 mm long and about 1.5 mm wide.

11. The apparatus of claim 10, wherein the total resistance of each line is about 7.7 Ohms.

12. The apparatus of claim 11, wherein a surface temperature of the heating element is above a superheat limit of a liquid inside the chamber to induce bubble nucleation.

13. The apparatus of claim 9, wherein the resistor is formed from platinum.

14. The apparatus of claim 13, wherein the resistor is about 3–6 microns wide, and about 500–3000 microns long.

15. The apparatus of claim 14, wherein the resistor has a roughened surface to induce bubble nucleation.

16. The apparatus of claim 15, wherein a surface temperature of the resistor is sufficient to induce bubble nucleation.

17. The apparatus of claim 16, wherein the surface temperature of the resistor is about 100° C. to about 280° C.

18. The apparatus of claim 13, wherein the resistor contains at least one hole for inducing bubble nucleation therein.

19. The apparatus of claim 8, wherein the bubble is about 200 microns in diameter.

20. Method of making a cell sorting apparatus, comprising the steps of:
forming a well on one surface of a first substrate, the well being configured and dimensioned to hold a single cell;
forming a chamber on an opposite surface of the first substrate;
forming a channel in the first substrate to connect the well and chamber together and permit fluid communication there between;
forming a heating element on a second substrate;
positioning the heating element under the chamber; and
attaching the first substrate onto the second substrate such that the second substrate forms the bottom of the chamber.

21. The method of claim 20, wherein the steps of forming the well, channel and chamber further comprise etching the first substrate.

22. The method of claim 21, wherein the first substrate comprises a silicon wafer.

23. The method of claim 21, wherein the steps of etching further comprise:
growing thermal oxide onto a first surface of a the silicon wafer substrate;
patterning the oxide using a first mask that defines the shape of the well;
spinning photoresist on top of the oxide;
patterning the oxide using a second mask that defines the shape of the channel;
etching the wafer to form the channel using the second mask;
etching the wafer to form the well using the first mask;
depositing photoresist on an opposite surface of the silicon wafer substrate;
patterning the photoresist using a third mask that defines the shape of the chamber; and
etching the wafer to form the chamber, the chamber having sufficient depth to connect with the channel.

24. The method of claim 20, wherein the step of forming the heating element comprises:
spinning photoresist onto the second substrate;
patterning the photoresist with a mask that defines the shape of a heating element;
selectively removing the photoresist to expose a region of the second substrate in the shape of the heating element; and
depositing a metallic conductor on the exposed region.

25. The method of claim 24, wherein the step of depositing a metallic conductor further comprises:
evaporating at least one metal onto the second substrate; and
selectively removing the metal from the substrate.

26. The method of claim 25, wherein the step of selectively removing the metal further comprises treating the substrate with acetone to remove excess photoresist and metal deposited on the photoresist.

27. The method of claim 20, wherein the second substrate comprises glass.

28. The method of claim 20, wherein the step of attaching the first substrate onto the second substrate further comprises joining the first and second substrates together with an adhesive.

29. A cell sorting apparatus for manipulation of cells comprising:

an array of geometric sites arranged across a substrate in a defined pattern, each site being dimensioned and configured to hold a single cell, wherein each site includes a capture mechanism comprising a non-uniform electric field trap that is capable of producing a potential energy well for selectively capturing the single cell, and a release mechanism for selectively releasing the single cell from the site.

30. The apparatus of claim 29, wherein the electric field trap comprises electrodes arranged in a trapezoidal configuration.

31. The apparatus of claim 29, wherein the electric field trap is three-dimensional.

32. The apparatus of claim 29, wherein the electrodes are thin-film poles.

33. The apparatus of claim 29, wherein the electrodes are formed from gold.

34. The apparatus of claim 29, wherein the release mechanism is configured to release the captured single cell by removing the potential energy well produced by the non-uniform electric field trap.

* * * * *

UNITED STATES PATENT AND TRADEMARK OFFICE
CERTIFICATE OF CORRECTION

PATENT NO. : 6,692,952 B1
APPLICATION NO. : 09/710032
DATED : February 17, 2004
INVENTOR(S) : Rebecca Braff et al.

It is certified that error appears in the above-identified patent and that said Letters Patent is hereby corrected as shown below:

Under Assignee:

Reads: Massachusetts Institute of Technology, Cambridge, MA (US)

Should Read: Massachusetts Institute of Technology, Cambridge, MA (US) and The General Hospital Corporation D/B/A Massachusetts General Hospital, Boston, MA (US)

Signed and Sealed this

Twenty-ninth Day of August, 2006

JON W. DUDAS
*Director of the United States Patent and Trademark Office*